(12) United States Patent
Miles et al.

(10) Patent No.: US 10,470,707 B2
(45) Date of Patent: Nov. 12, 2019

(54) SYSTEM AND METHODS FOR PERFORMING PERCUTANEOUS PEDICLE INTEGRITY ASSESSMENTS

(75) Inventors: Patrick Miles, San Diego, CA (US);
Scot Martinelli, Mountain Top, PA (US); Eric Finley, Poway, CA (US); Jamil Elbanna, San Diego, CA (US); James Gharib, San Diego, CA (US); Allen Farquhar, San Diego, CA (US); Norbert Kaula, Arvada, CO (US); Jeffrey Blewett, San Diego, CA (US); Goretti Medeiros, legal representative, Plantsville, CT (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 12/427,612

(22) Filed: Apr. 21, 2009

(65) Prior Publication Data
US 2009/0204176 A1  Aug. 13, 2009

Related U.S. Application Data

(63) Continuation of application No. 10/836,105, filed on Apr. 30, 2004, now Pat. No. 7,664,544, which is a
(Continued)

(51) Int. Cl.
| | |
|---|---|
| *A61B 5/00* | (2006.01) |
| *A61B 5/0488* | (2006.01) |
| *A61B 5/05* | (2006.01) |
| *A61B 5/11* | (2006.01) |
| *A61N 1/08* | (2006.01) |

(Continued)

(52) U.S. Cl.
CPC .......... *A61B 5/4893* (2013.01); *A61B 5/0488* (2013.01); *A61B 5/05* (2013.01); *A61B 5/1106* (2013.01); *A61N 1/08* (2013.01); *A61B 5/04001* (2013.01); *A61B 5/1104* (2013.01); *A61B 5/6823* (2013.01); *A61B 17/1626* (2013.01); *A61B 17/1655* (2013.01); *A61B 17/1671* (2013.01); *A61B 17/1757* (2013.01); *A61B 2505/05* (2013.01); *A61N 1/36014* (2013.01)

(58) Field of Classification Search
CPC ....... A61B 5/0488; A61B 5/05; A61B 5/1106; A61N 1/08; A61N 1/36014
USPC ............. 600/600, 601, 564, 554; 606/61, 72
See application file for complete search history.

(56) References Cited

U.S. PATENT DOCUMENTS

| | | |
|---|---|---|
| 208,227 A | 9/1878 | Dorr |
| 1,548,184 A | 8/1925 | Cameron |

(Continued)

FOREIGN PATENT DOCUMENTS

| | | |
|---|---|---|
| DE | 4445593 | 6/1996 |
| DE | 29908259 | 7/1999 |

(Continued)

OTHER PUBLICATIONS

Merriam-Webster's Collegiate Dictionary, Merriam-Webster, Incorporated, 10th ed, 860.*
(Continued)

*Primary Examiner* — Sean P Dougherty

(57) ABSTRACT

The present invention involves systems and related methods for performing percutaneous pedicle integrity assessments involving the use of neurophysiology.

12 Claims, 28 Drawing Sheets

Related U.S. Application Data continuation of application No. PCT/US02/35047, filed on Oct. 30, 2002.

(60) Provisional application No. 60/336,501, filed on Oct. 30, 2001.

(51) Int. Cl.
*A61B 5/04* (2006.01)
*A61B 17/16* (2006.01)
*A61B 17/17* (2006.01)
*A61N 1/36* (2006.01)

(56) References Cited

U.S. PATENT DOCUMENTS

| | | | |
|---|---|---|---|
| 2,704,064 A | 3/1955 | Fizzell et al. | |
| 2,736,002 A | 2/1956 | Oriel | |
| 2,808,826 A | 10/1957 | Reiner et al. | |
| 3,364,929 A | 1/1968 | Ide et al. | |
| 3,664,329 A | 5/1972 | Naylor | |
| 3,682,162 A | 8/1972 | Colyer | |
| 3,785,368 A | 1/1974 | McCarthy et al. | |
| 3,830,226 A | 8/1974 | Staud et al. | |
| 3,851,641 A | 12/1974 | Toole et al. | |
| 3,957,036 A | 5/1976 | Normann | |
| 4,099,519 A | 7/1978 | Warren | |
| 4,164,214 A | 8/1979 | Stark et al. | |
| 4,207,897 A | 6/1980 | Lloyd et al. | |
| 4,224,949 A | 9/1980 | Scott et al. | |
| 4,235,242 A | 11/1980 | Howson et al. | |
| 4,252,130 A | 2/1981 | Pivery et al. | |
| 4,285,347 A | 8/1981 | Hess | |
| 4,291,705 A | 9/1981 | Severinghaus et al. | |
| 4,461,300 A | 7/1984 | Christensen | |
| 4,515,168 A | 5/1985 | Chester et al. | |
| 4,519,403 A | 5/1985 | Dickhudy | |
| 4,545,374 A | 10/1985 | Jacobson | |
| 4,561,445 A | 12/1985 | Berke et al. | |
| 4,562,832 A | 1/1986 | Wilder et al. | |
| 4,573,448 A | 3/1986 | Kambin | |
| 4,592,369 A | 6/1986 | Davis et al. | |
| 4,595,018 A | 6/1986 | Rantala | |
| 4,633,889 A | 1/1987 | Talalla | |
| 4,658,835 A | 4/1987 | Pohndorf | |
| 4,744,371 A | 5/1988 | Harris | |
| 4,759,377 A | 7/1988 | Dykstra | |
| 4,807,642 A | 2/1989 | Brown | |
| 4,892,105 A | 1/1990 | Prass | |
| 4,926,865 A | 5/1990 | Oman | |
| 4,962,766 A | 10/1990 | Herzon | |
| 4,964,411 A | 10/1990 | Johnson et al. | |
| 5,007,902 A | 4/1991 | Will | |
| 5,058,602 A | 10/1991 | Brody | |
| 5,081,990 A | 1/1992 | Deletis | |
| 5,092,344 A | 3/1992 | Lee | |
| 5,127,403 A | 7/1992 | Brownie | |
| 5,161,533 A | 11/1992 | Prass et al. | |
| 5,196,015 A * | 3/1993 | Neubardt | A61B 17/8875 600/554 |
| RE34,390 E | 9/1993 | Culver | |
| 5,255,691 A | 10/1993 | Otten | |
| 5,282,468 A | 2/1994 | Klepinski | |
| 5,284,153 A | 2/1994 | Raymond et al. | |
| 5,284,154 A | 2/1994 | Raymond et al. | |
| 5,299,563 A | 4/1994 | Seton | |
| 5,312,417 A | 5/1994 | Wilk | |
| 5,313,956 A | 5/1994 | Knuttson et al. | |
| 5,327,902 A | 7/1994 | Lemmen | |
| 5,333,618 A | 8/1994 | Lekhtman et al. | |
| 5,375,067 A | 12/1994 | Berchin | |
| 5,383,876 A | 1/1995 | Nardella | |
| 5,388,587 A * | 2/1995 | Knutsson | A61B 5/04001 600/545 |
| 5,450,845 A | 9/1995 | Axelgaard | |
| 5,474,558 A * | 12/1995 | Neubardt | A61B 17/8875 600/554 |
| 5,480,440 A | 1/1996 | Kambin | |
| 5,482,038 A | 1/1996 | Ruff | |
| 5,484,437 A | 1/1996 | Michelson | |
| 5,540,235 A | 7/1996 | Wilson | |
| 5,549,656 A | 8/1996 | Reiss | |
| 5,560,372 A | 10/1996 | Cory | |
| 5,566,678 A | 10/1996 | Cadwell | |
| 5,579,781 A | 12/1996 | Cooke | |
| 5,593,429 A | 1/1997 | Ruff | |
| 5,599,279 A | 2/1997 | Slotman | |
| 5,630,813 A | 5/1997 | Kieturakis | |
| 5,671,752 A | 9/1997 | Sinderby et al. | |
| 5,707,359 A | 1/1998 | Bufalini | |
| 5,711,307 A | 1/1998 | Smits | |
| 5,741,253 A | 4/1998 | Michelson | |
| 5,779,642 A | 4/1998 | Nightengale | |
| 5,759,159 A | 6/1998 | Masreliez | |
| 5,772,661 A | 6/1998 | Michelson | |
| 5,775,331 A | 7/1998 | Raymond et al. | |
| 5,785,658 A | 7/1998 | Benaron | |
| 5,797,854 A | 8/1998 | Hedgecock | |
| 5,806,522 A | 9/1998 | Katims | |
| 5,807,272 A | 9/1998 | Kun et al. | |
| 5,814,073 A | 9/1998 | Bonutti | |
| 5,830,151 A | 11/1998 | Hadzic et al. | |
| 5,851,191 A | 12/1998 | Gozani | |
| 5,853,373 A | 12/1998 | Griffith et al. | |
| 5,860,973 A | 1/1999 | Michelson | |
| 5,862,314 A | 1/1999 | Jeddeloh | |
| 5,872,314 A | 2/1999 | Clinton | |
| 5,885,219 A | 3/1999 | Nightengale | |
| 5,888,196 A | 3/1999 | Bonutti | |
| 5,902,231 A | 5/1999 | Foley et al. | |
| 5,928,139 A | 7/1999 | Koros | |
| 5,928,158 A | 7/1999 | Aristides | |
| 5,928,159 A | 7/1999 | Eggers et al. | |
| 5,938,688 A | 8/1999 | Schiff | |
| 5,947,964 A | 9/1999 | Eggers et al. | |
| 5,976,094 A | 11/1999 | Gozani et al. | |
| 6,004,262 A | 12/1999 | Putz et al. | |
| 6,026,323 A | 2/2000 | Skladnev et al. | |
| 6,027,456 A | 2/2000 | Feler et al. | |
| 6,038,469 A | 3/2000 | Karisson et al. | |
| 6,038,477 A | 3/2000 | Kayyali | |
| 6,050,992 A | 4/2000 | Nichols | |
| 6,074,343 A | 6/2000 | Nathanson et al. | |
| 6,104,957 A | 8/2000 | Alo et al. | |
| 6,104,960 A | 8/2000 | Duysens et al. | |
| 6,119,068 A | 9/2000 | Kannonji | |
| 6,120,503 A | 9/2000 | Michelson | |
| 6,122,547 A * | 9/2000 | Benja-Athon | 607/46 |
| 6,128,576 A | 10/2000 | Nichimoto et al. | |
| 6,132,386 A | 10/2000 | Gozani et al. | |
| 6,132,387 A | 10/2000 | Gozani et al. | |
| 6,135,965 A | 10/2000 | Tumer et al. | |
| 6,139,493 A | 10/2000 | Koros | |
| 6,146,335 A | 11/2000 | Gozani | |
| 6,161,047 A | 12/2000 | King et al. | |
| 6,181,961 B1 | 1/2001 | Prass | |
| 6,206,826 B1 | 3/2001 | Mathews et al. | |
| 6,224,549 B1 | 5/2001 | Drongelen | |
| 6,259,945 B1 | 7/2001 | Epstein et al. | |
| 6,266,558 B1 | 7/2001 | Gozani et al. | |
| 6,292,701 B1 | 9/2001 | Prass et al. | |
| 6,306,100 B1 | 10/2001 | Prass | |
| 6,312,392 B1 | 11/2001 | Herzon | |
| 6,325,764 B1 | 12/2001 | Griffith et al. | |
| 6,334,068 B1 | 12/2001 | Hacker | |
| 6,337,994 B1 | 1/2002 | Stoianovici et al. | |
| 6,425,859 B1 | 7/2002 | Foley et al. | |
| 6,425,901 B1 | 7/2002 | Zhu et al. | |
| 6,451,015 B1 | 9/2002 | Rittman, III et al. | |
| 6,466,817 B1 * | 10/2002 | Kaula | A61B 5/04001 600/546 |
| 6,478,793 B1 * | 11/2002 | Cosman | A61B 18/1477 128/898 |
| 6,493,588 B1 * | 12/2002 | Malaney et al. | 607/46 |

(56) References Cited

U.S. PATENT DOCUMENTS

| | | |
|---|---|---|
| 6,500,128 B2 | 12/2002 | Marino |
| 6,535,759 B1 | 3/2003 | Epstein et al. |
| 6,564,078 B1 | 5/2003 | Marino et al. |
| 6,579,244 B2 | 6/2003 | Goodwin |
| 6,719,692 B2 | 4/2004 | Kleffner et al. |
| 6,760,616 B2 | 7/2004 | Hoey et al. |
| 6,796,985 B2 | 9/2004 | Bolger et al. |
| 6,819,956 B2 | 11/2004 | DiLorenzo |
| 6,829,508 B2 | 12/2004 | Schulman et al. |
| 6,849,047 B2 | 2/2005 | Goodwin |
| 6,855,105 B2 | 2/2005 | Jackson, III et al. |
| 6,902,569 B2 | 6/2005 | Parmer et al. |
| 6,926,728 B2 | 8/2005 | Zucherman et al. |
| 6,929,606 B2 | 8/2005 | Ritland |
| 7,047,082 B1 | 5/2006 | Schrom et al. |
| 7,050,848 B2 | 5/2006 | Hoey et al. |
| 7,079,883 B2 | 7/2006 | Marino et al. |
| 7,089,059 B1 | 8/2006 | Pless |
| 7,177,677 B2 | 2/2007 | Kaula et al. |
| 7,207,949 B2 | 4/2007 | Miles et al. |
| 7,470,236 B1* | 12/2008 | Kelleher ............ A61B 5/04001 |
| 2001/0039949 A1 | 11/2001 | Loubser |
| 2001/0056280 A1 | 12/2001 | Underwood et al. |
| 2002/0007129 A1 | 1/2002 | Marino |
| 2002/0072686 A1 | 6/2002 | Hoey et al. |
| 2002/0123780 A1 | 9/2002 | Grill et al. |
| 2002/0161415 A1 | 10/2002 | Cohen |
| 2002/0193843 A1 | 12/2002 | Hill et al. |
| 2003/0105503 A1 | 6/2003 | Marino |
| 2004/0199084 A1 | 10/2004 | Kelleher et al. |
| 2004/0225228 A1 | 11/2004 | Ferree |
| 2005/0004593 A1 | 1/2005 | Simonson |
| 2005/0004623 A1 | 1/2005 | Miles et al. |
| 2005/0033380 A1 | 2/2005 | Tanner et al. |
| 2005/0075578 A1 | 4/2005 | Gharib et al. |
| 2005/0149035 A1 | 7/2005 | Pimentra et al. |
| 2005/0182454 A1 | 8/2005 | Gharib et al. |
| 2005/0192575 A1 | 9/2005 | Pacheco |
| 2006/0025703 A1 | 2/2006 | Miles et al. |
| 2006/0052828 A1 | 3/2006 | Kim et al. |
| 2006/0069315 A1 | 3/2006 | Miles et al. |
| 2006/0224078 A1 | 10/2006 | Hoey et al. |
| 2007/0016097 A1 | 1/2007 | Farquhar et al. |
| 2007/0198062 A1 | 8/2007 | Miles et al. |
| 2007/0293782 A1 | 12/2007 | Marino |
| 2008/0058606 A1 | 3/2008 | Miles et al. |
| 2008/0064976 A1 | 3/2008 | Kelleher et al. |
| 2008/0064977 A1 | 3/2008 | Kelleher et al. |
| 2008/0065178 A1 | 3/2008 | Kelleher et al. |
| 2008/0071191 A1 | 3/2008 | Kelleher et al. |

FOREIGN PATENT DOCUMENTS

| | | |
|---|---|---|
| EP | 0607688 | 7/1994 |
| EP | 0972538 | 1/2000 |
| EP | 1146816 | 10/2001 |
| FR | 2795624 | 1/2001 |
| JP | 2001170190 | 6/2001 |
| JP | 2001299718 | 10/2001 |
| JP | 11076430 | 3/2009 |
| WO | WO 97/11638 | 4/1997 |
| WO | WO 00/19894 | 4/2000 |
| WO | WO 00/66217 | 11/2000 |
| WO | WO 00/67645 | 11/2000 |
| WO | WO 01/03604 | 1/2001 |
| WO | WO 01/37728 | 5/2001 |
| WO | WO 03/026482 | 4/2003 |
| WO | WO 03/037170 | 5/2003 |
| WO | WO 05/013805 | 2/2005 |

OTHER PUBLICATIONS

Anderson et al., "Pedicle screws with high electrical resistance: a potential source of error with stimulus-evoked EMG," *Spine*, Department of Orthopaedic Surgery University of Virginia, Jul. 15, 2002, 27(14): 1577-1581.

Bose et al., "Neurophysiologic Monitoring of Spinal Nerve Root Function During Instrumented Posterior Lumber Spine Surgery," *Spine*, 2002, 27(13):1444-1450.

Brackmann II EMG System, Medical Electronics, 1999, 4 pages.

Calancie et al., "Stimulus-Evoked EMG Monitoring During Transpedicular Lumbosacral Spine Instrumentation" *Spine*, 1994, 19(24): 2780-2786.

Clements et al., "Evoked and Spontaneous Electromyography to Evaluate Lumbosacral Pedicle Screw Placement," *Spine*, 1996, 21(5): 600-604.

Danesh-Clough et al. ,"The Use of Evoked EMG in Detecting Misplaced Thoracolumbar Pedicle Screws," *Spine*, Orthopaedic Department Dunedin Hospital, Jun. 15, 2001, 26(12): 1313-1316.

Darden et al., "A Comparison of Impedance and Electromyogram Measurements in Detecting the Presence of Pedicle Wall Breakthrough," *Spine*, Charlotte Spine Center North Carolina, Jan. 15, 1998, 23(2): 256-262.

Ebraheim et al., "Anatomic Relations Between the Lumbar Pedicle and the Adjacent Neural Structures," *Spine*, Department of Orthopaedic Surgery Medical College of Ohio, Oct. 15, 1997, 22(20): 2338-2341.

"Electromyography System," International Search report from International Application No. PCT/US00/32329, Apr. 27, 2001, 9 pages.

Ford et al. "Electrical Characteristics of Peripheral Nerve Stimulators Implications for Nerve Localization," *Regional Anesthesia*, 1984, 9: 73-77.

Glassman et al., "A Prospective Analysis of Intraoperative Electromyographic Monitoring of Pedicle Screw Placement With Computed Tomographic Scan Confirmation," *Spine*, 1995, 20(12): 1375-1379.

Greenblatt et al., "Needle Nerve Stimulator—Locator: Nerve Blocks with a New Instrument for Locating Nerves," *Anesthesia& Analgesia*, 1962, 41(5): 599-602.

Haig et al., "The Relation Among Spinal Geometry on MRI, Paraspinal Electromyographic Abnormalities, and Age in Persons Referred for Electrodiagnostic Testing of Low Back Symptoms," *Spine*, Department of Physical Medicine and Rehabilitation University of Michigan, Sep. 1, 2002, 27(17): 1918-1925.

Haig, "Point of view," *Spine*, 2002, 27(24): 2819.

Holland et al., "Higher Electrical Stimulus Intensities are Required to Activate Chronically Compressed Nerve Roots: Implications for Intraoperative Electromyographic Pedicle Screw Testing," *Spine*, Department of Neurology, Johns Hopkins University School of Medicine, Jan. 15, 1998, 23/92): 224-227.

Holland, "Intraoperative Electromyography During Thoracolumbar Spinal Surgery," *Spine*, 1998, 23(17): 1915-1922.

Journee, H.L. et al., "System for Intra-Operative Monitoring of the Cortical Integrity of the Pedicle During Screw Placement in Low-Back Surgery: Design and Clinical Results," *Sensory and neuromuscular diagnostic instrumentation and data analysis, 18th Annual International Conference on Engineering in Medicine and Biology Society*,1 (31), Oct. 1996, 144-145.

Lenke et al., "Triggered Electromyographic Threshold for Accuracy of Pedicle Screw Placement," *Spine*, 1995, 20(4): 1585-1591.

Maguire et al., "Evaluation of Intrapedicular Screw Position Using Intraoperative Evoked Electromyography," *Spine*, 1995, 20(9): 1068-1074.

Martin et al. "Initiation of Erection and Semen Release by Rectal Probe Electrostimulation (RPE)," *The Journal of Urology*, The Williams& Wilkins Co., 1983, 129: 637-642.

Minahan et al., "The Effect of Neuromuscular Blockade on Pedicle Screw Stimulation Thresholds" *Spine*, Department of Neurology, Johns Hopkins University School of Medicine, Oct. 1, 2000, 25(19): 2526-2530.

"Nerve Proximity and Status Detection System and Method," International Search Report from International Application No. PCT/US01/18606, Oct. 18, 2001, 6 pages.

"Neurovision SE Nerve Locator/Monitor", RLN Systems Inc. Operators Manual, 1999, 22 pages.

(56) References Cited

OTHER PUBLICATIONS

Pither et al., "The Use of Peripheral Nerve Stimulators for Regional Anesthesia: Review of Experimental Characteristics Technique and Clinical Applications," *Regional Anesthesia*, 1985, 10:49-58.

Raj et al., "Infraclavicular Brachial Plexus Block—A New Approach" *Anesthesia and Analgesia*, 1973, (52)6: 897-904.

Raj et al., "The Use of Peripheral Nerve Stimulators for Regional Anesthesia," *Clinical Issues in Regional Anesthesia*, 1985, 1(4):1-6.

Raj et al., "Use of the Nerve Stimulator for Peripheral Blocks," *Regional Anesthesia*, Apr.-Jun. 1980, pp. 14-21.

Raymond et al., "The Nerve Seeker: A System for Automated Nerve Localization," *Regional Anesthesia*, 1992, 17(3): 151-162.

"Relative Nerve Movement and Status Detection System and Method," International Search Report from International Application No. PCT/US01/18579, dated Jan. 15, 2002, 6 pages.

Shafik, "Cavernous Nerve Simulation through an Extrapelvic Subpubic Approach: Role in Penile Erection," *Eur. Urol*, 1994, 26: 98-102.

"System and Method for Determining Nerve Proximity Direction and Pathology During Surgery," International Search Report from International Application No. PCT/US02/22247, dated Mar. 27, 2003, 4 pages.

"System and Methods for Determining Nerve Direction to a Surgical Instrument," International Search Report from International Application No. PCT/US03/02056, dated Aug. 12, 2003, 5 pages.

"Systems and Methods for Performing Percutaneous Pedicle Integrity Assessments," International Search Report from International Application No. PCT/US02/35047, dated Aug. 11, 2003, 5 pages.

"Systems and Methods for Performing Surgery Procedures and Assessments," International Search Report from International Application No. PCT/US02/30617, dated Jun. 5, 2003, 4 pages.

"The Brackmann II EMG Monitoring System," Medical Electronics Co. Operator's Manual Version 1.1, 1995, 50 pages.

"The Nicolet Viking IV," Nicolet Biomedical Products, 1999, 6 pages.

Toleikis et al., "The Usefulness of Electrical Stimulation for Assessing Pedicle Screw Replacements," *Journal of Spinal Disorder*, 2000, 13(4): 283-289.

Welch et al., "Evaluation with evoked and spontaneous electromyography during lumbar instrumentation: a prospective study," *J. Neurosurg.* 87, 1997, pp. 397-402.

Australian Application No. AU 2002353954, Official Examination Letter dated Nov. 27, 2006.

Australian Application No. AU 2002353954, Response to Official Examination Letter dated Jan. 25, 2008.

Australian Application No. AU 2002353954, Official Examination Letter dated Feb. 1, 2008.

European Application No. EP 02789358.5, Official Examination Letter dated Nov. 27, 2007.

European Application No. EP 02789358.5, Response to Official Examination Letter dated May 23, 2008.

Kim, et al., "Comparison of Multifidus Muscle Atrophy and Trunk Extension Muscle Strength: Percutaneous Versus Open Pedicle Screw Fixation," *Spine* 30(1): 123-129, 2005.

Preminger, et al., "Percutaneous Nephrostolithotomy vs. Open Surgery for Renal Calculi: a Comparative Study," JAMA 254(8): 1054-1058, 1985.

Gilberts, et al., "Prospective Randomized Trial of Open Versus Percutaneous Surgery for Trigger Digits," The Journal of Hand Surgery 26A(3): 497-499, 2001.

Cardoso, et al., "Comparison Between Percutaneous Balloon Valvuloplasty and Open Commissurotomy for Mitral Stenosis," Cardiology 98: 186-190, 2002.

Wiesner, et al., "Clinical Evaluation and Computed Tomography Scan Analysis of Screw Tracts after Percutaneous Insertion of Pedicle Screw in the Lumbar Spine," *Spine* 25(5): 615-621, 2000.

Foley, et al., "Percutaneous Pedicle Fixation of the Lumbar Spine," Neurosurg Focus 10(4): Article 10, 2001.

* cited by examiner

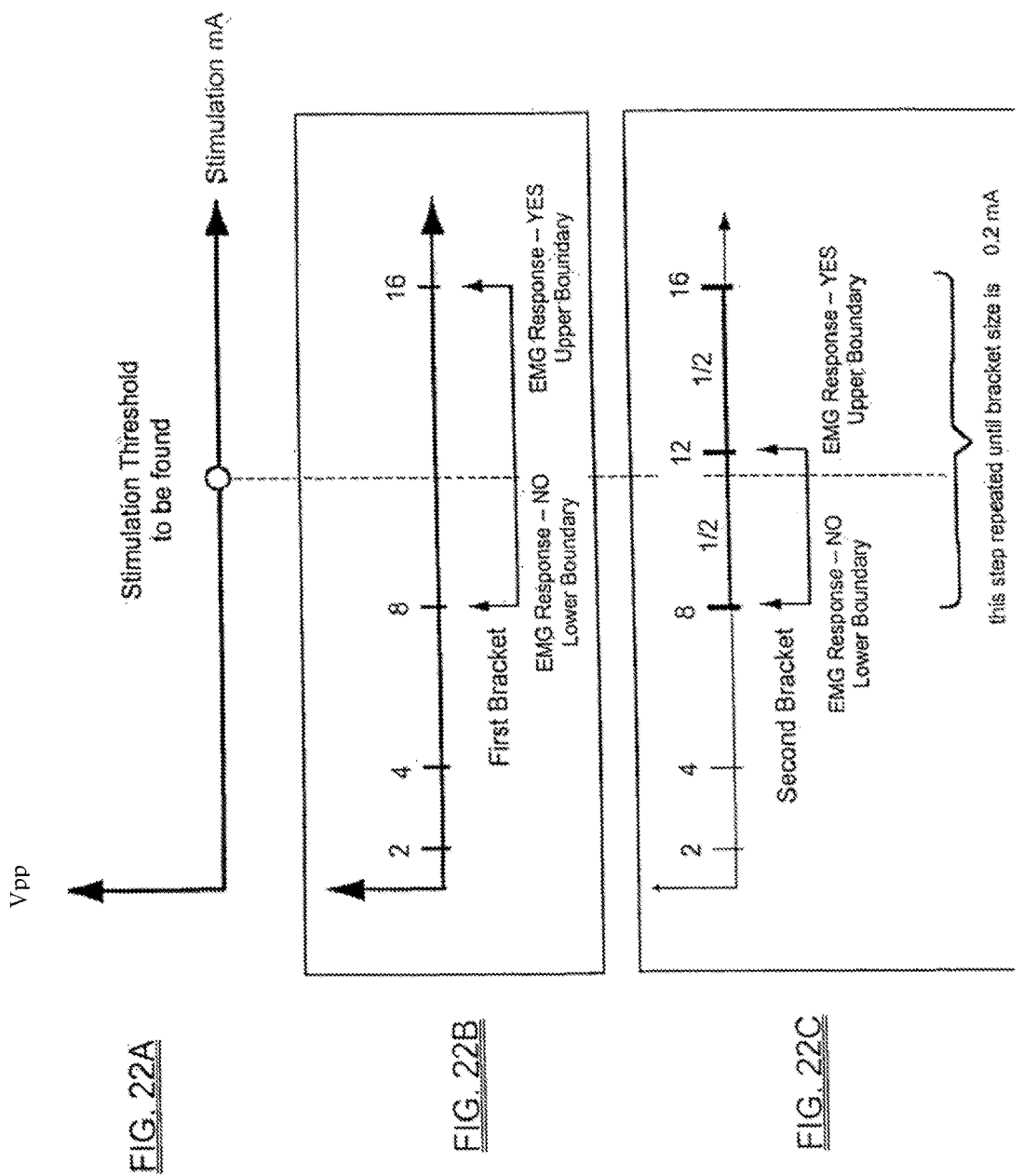

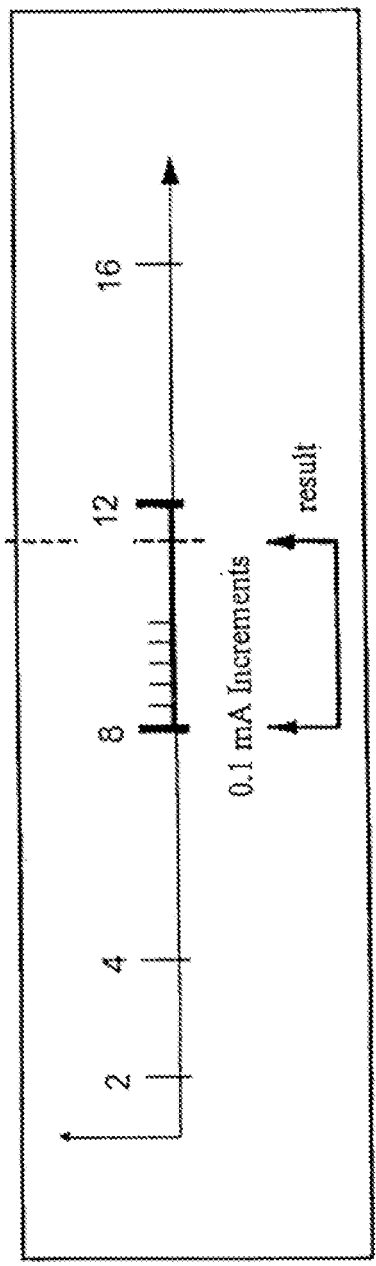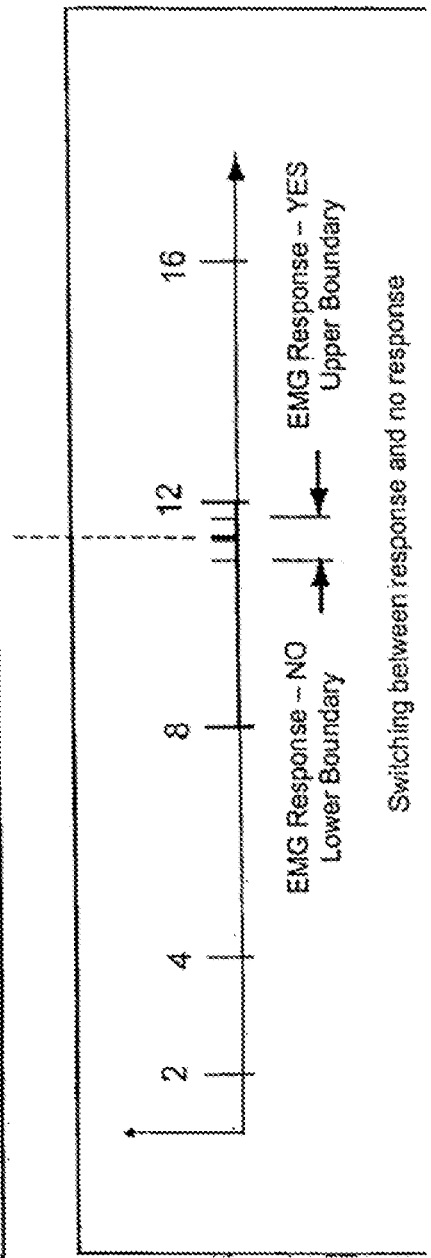
FIG. 22D
FIG. 22E

SYSTEM AND METHODS FOR PERFORMING PERCUTANEOUS PEDICLE INTEGRITY ASSESSMENTS

CROSS-REFERENCES TO RELATED APPLICATIONS

This is a continuation of U.S. patent application Ser. No. 10/836,105 filed on Apr. 30, 2004 by Miles et al., which is a continuation of PCT Application No. PCT/US02/35047 filed on Oct. 30, 2002 and published on May 8, 2003 as PCT Pub. No. WO03/037170, which claims priority to U.S. Provisional Patent Application 60/336,501 entitled "Spinal Surgery Systems and Methods" filed Oct. 30, 2001, the entire contents of which are hereby expressly incorporated by reference into this disclosure as if set forth fully herein.

BACKGROUND OF THE INVENTION

I. Field of the Invention

The present invention relates to a system and methods generally aimed at surgery. More particularly, the present invention is directed at a system and related methods for performing percutaneous pedicle integrity assessments involving the use of neurophysiology.

II. Description of Related Art

A trend in spinal surgery is toward performing surgery in a minimally invasive or minimal access fashion to avoid the trauma of so-called open or "direct access" procedures. A specific area of interest is in the percutaneous placement of pedicle screws, which are typically employed to effect posterior fixation in spinal fusion procedures. While great strides are being made in this area, a risk exists (as it does in open procedures) that the pedicle may become breached, cracked, or otherwise compromised due to the formation and/or preparation of the pilot hole (designed to receive a pedicle screw) and/or due to the introduction of the pedicle screw into the pilot hole. If the pedicle (or more specifically, the cortex of the medial wall, lateral wall, superior wall and/or inferior wall) is breached, cracked, or otherwise compromised, the patient may experience pain or neurologic deficit due to unwanted contact between the pedicle screw and exiting nerve roots. This oftentimes necessitates revision surgery, which is disadvantageously painful for the patient and costly, both in terms of recovery time and hospitalization.

Various attempts have been undertaken at performing pedicle integrity assessments. As used herein, the term "pedicle integrity assessment" is defined as detecting or otherwise determining whether a part of a pedicle has been breached, cracked, or otherwise compromised due to the formation and/or preparation of the pilot hole (designed to receive a pedicle screw) and/or due to the introduction of the pedicle screw into the pilot hole. "Formation" is defined as the act of creating an initial pilot hole in a pedicle, such as through the use of a drill or other hole-forming element. "Preparation" is defined as the act of refining or otherwise acting upon the interior of the pilot hole to further prepare it to receive a pedicle screw, such as by introducing a tap or reamer element into the initial pilot hole. "Introduction" is defined as the act of inserting or otherwise placing a pedicle screw into the initially formed and/or prepared pilot hole, such as by screwing the pedicle screw into the pilot hole via a screw driver or similar element.

Among the attempts, X-ray and other imaging systems have been employed, but these are typically quite expensive and are oftentimes limited in terms of resolution such that pedicle breaches may fail to be detected.

Still other attempts involve capitalizing on the insulating characteristics of bone (specifically, that of the medial wall of the pedicle) and the conductivity of the exiting nerve roots themselves. That is, if the medial wall of the pedicle is breached, a stimulation signal applied to the pedicle screw and/or the pilot hole (prior to screw introduction) will cause the various muscle groups coupled to the exiting nerve roots to contract. If the pedicle wall has not been breached, the insulating nature of the pedicle will prevent the stimulation signal from innervating the given nerve roots such that the associated muscle groups will not twitch. Traditional EMG monitoring systems may be employed to augment the ability to detect such innervation. A drawback with such prior art systems is that they do not lend themselves to assessing pedicle integrity in cases where pedicle screws are placed in a percutaneous fashion, such as may be accomplished by any number of commercially available percutaneous pedicle screw implantation systems. With the anticipated increase in the number of such percutaneous pedicle screw procedures, a significant number of patients will be at risk of having misplaced pedicle screws given the lack of a percutaneous manner of performing pedicle integrity assessments.

The present invention is directed at addressing this need and eliminating, or at least reducing, the effects of the shortcomings of the prior art as described above.

SUMMARY OF THE INVENTION

The present invention overcomes the drawbacks of the prior art by providing, according to a first broad aspect of the present invention, a system for performing percutaneous pedicle integrity assessments comprising the steps of: (a) percutaneously introducing an insulation member to a pedicle target site; (b) establishing electrical communication between a stimulation element and an interior of a pedicle screw pilot hole; (c) applying a stimulation signal to said stimulation element; and (d) monitoring to assess whether nerves adjacent said pedicle are innervating as a result of the step of applying said application of stimulation signal to said stimulation element.

The present invention overcomes the drawbacks of the prior art by providing, according to a second broad aspect of the present invention, a method for performing percutaneous pedicle integrity assessments comprising the steps of: (a) percutaneously introducing an insulated K-wire into contact with at least one of a pedicle screw and a pedicle screw pilot hole; (b) applying a stimulation signal to said K-wire; and (c) monitoring to assess whether nerves adjacent said pedicle are innervating as a result of the step of applying said stimulation signal to said K-wire.

The present invention overcomes the drawbacks of the prior art by providing, according to a third broad aspect of the present invention, a method for performing percutaneous pedicle integrity assessments comprising the steps of: (a) percutaneously introducing an insulated member to the approximate opening of a pedicle screw pilot hole; (b) introducing a pedicle screw pilot hole preparation tool through said insulated member to prepare said pedicle screw pilot hole; (c) applying a stimulation signal to said pedicle screw pilot hole preparation tool; and (d) monitoring to assess whether nerves adjacent said pedicle are innervating as a result of the step of applying said stimulation signal to said pedicle screw pilot hole preparation tool.

The present invention overcomes the drawbacks of the prior art by providing, according to a fourth broad aspect of the present invention, a method for performing percutaneous pedicle integrity assessments comprising the steps of: (a) percutaneously introducing an insulated K-wire into contact with a pedicle screw pilot hole; (b) applying a stimulation signal to said K-wire; (c) monitoring to assess whether nerves adjacent said pedicle are innervating as a result of the step of applying said stimulation signal to said K-wire; (d) percutaneously introducing an insulated member to the approximate opening of a pedicle screw pilot hole; (e) introducing a tap member through said insulated member to prepare said pedicle screw pilot hole; (f) applying a stimulation signal to said tap member; and (g) monitoring to assess whether nerves adjacent said pedicle are innervating as a result of the step of applying said stimulation signal to said tap member.

The present invention overcomes the drawbacks of the prior art by providing, according to a fifth broad aspect of the present invention, a system for performing percutaneous pedicle integrity assessments including a body and a stimulation source. The body having an aperture dimensioned to receive a stimulation element therethrough and an insulation region capable of being percutaneously introduced to a pedicle target site within a patient. The stimulation source in electrical communication with said stimulation element for selectively applying a stimulation signal to said stimulation element to assess whether nerves adjacent said pedicle target site innervate as a result of applying said stimulation signal to said stimulation element.

But for the systems and methods of the present invention, patients may be released and subsequently experience pain and/or neurologic deficit due to unwanted contact between the exiting nerve root and misplaced pedicle screws, which oftentimes requires another costly and painful surgery.

BRIEF DESCRIPTION OF THE DRAWINGS

FIGS. 22A-22E are graphs illustrating a current threshold-hunting algorithm according to one embodiment of the present invention;

DESCRIPTION OF THE SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems disclosed herein boast a variety of inventive features and components that warrant patent protection, both individually and in combination.

Figure 1:
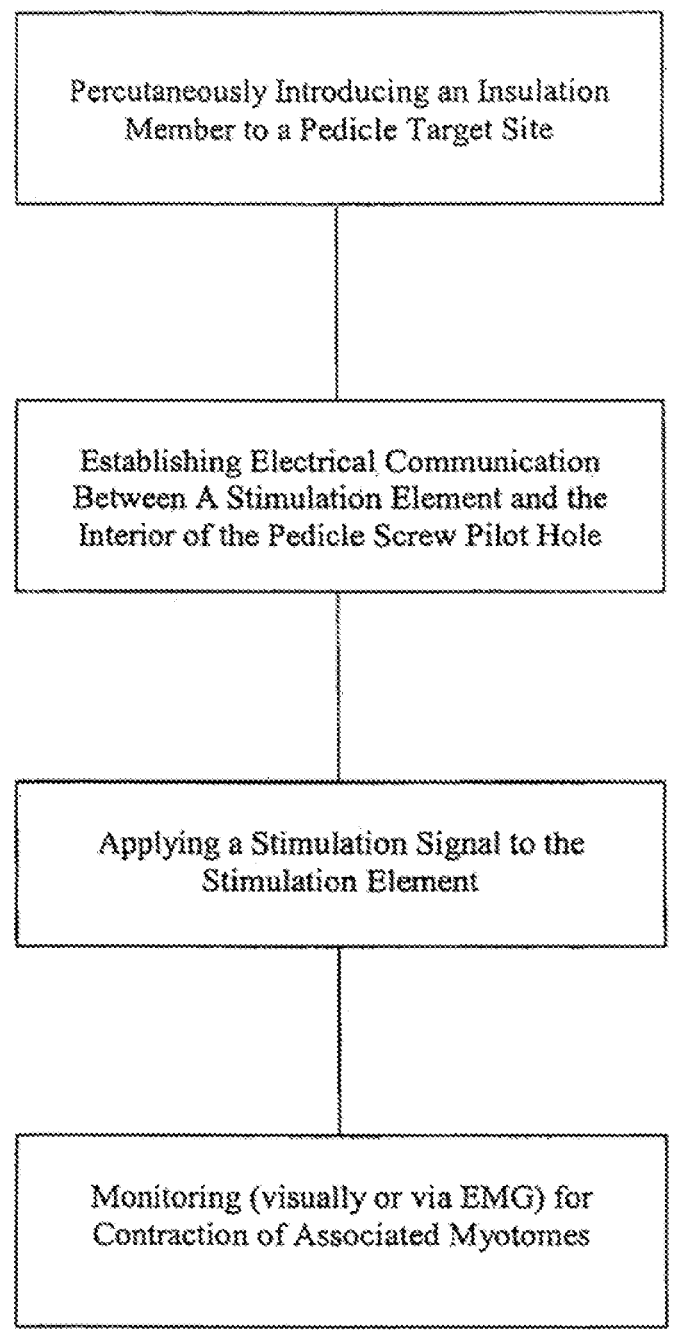
FIG. 1 is a flow chart illustrating the fundamental steps of the percutaneous pedicle integrity assessment system according to the present invention.

The present invention is directed at performing percutaneous pedicle integrity assessments. FIG. 1 illustrates the fundamental method steps according to the present invention, namely: (a) percutaneously introducing an insulation member to a pedicle target site; (b) establishing electrical communication between a stimulation element and an interior of a pedicle screw pilot hole; (c) applying a stimulation signal to the stimulation element; and (d) monitoring to assess whether nerves adjacent the pedicle are innervating as a result of the step of applying the stimulation signal to the stimulation element.

The step of percutaneously introducing an insulation member to a pedicle target site may be accomplished in any of a variety of suitable fashions, including but not limited to providing the insulation member as a tubular insulation member dimensioned to receive and pass through at least one of a K-wire and a pedicle screw pilot hole preparation tool, such as a tap member. It may also be accomplished by providing a K-wire having an insulated coating with an exposed, electrically conductive distal end, as well as a tap member having an insulated coating with an exposed, electrically conductive threaded region. The pedicle target site may, by way of example only, comprise at least one of a fully inserted pedicle screw and the opening of at least one of an initially formed pedicle screw pilot hole and a prepared pedicle screw pilot hole, depending upon the insulation member employed.

The step of establishing electrical communication between a stimulation element and an interior of a pedicle screw pilot hole may be accomplished in any of a variety of suitable fashions, including but not limited to disposing a K-wire through a K-wire insulator such that a distal tip of the K-wire contacts a fully inserted pedicle screw, which itself is in electrical communication with the interior of the pedicle screw pilot hole. It may also be accomplished by disposing a K-wire through a K-wire insulator such that the distal tip of the K-wire contacts the interior of the pedicle screw pilot hole. In yet another exemplary embodiment, it may be accomplished by bringing a stimulation element (such as a K-wire and/or electrical coupling device) into contact with a tap member disposed through the insulation member. When a K-wire constitutes the stimulation element, it may be useful to provide the tap member with a longitudinal lumen for receiving and passing the K-wire therethrough to establish electrical communication therebetween.

The step of applying a stimulation signal to the stimulation element may be accomplished in any number of suitable fashions, including but not limited to applying voltage and/or current pulses of varying magnitude and/or frequency to the stimulation element. In a preferred embodiment, the stimulation signal may be applied to the stimulation element after the initial pilot hole has been formed, after the pilot hole has been prepared (such as with a tap member) and/or after the pedicle screw has been fully inserted into the pilot hole.

The step of monitoring to assess whether nerves adjacent the pedicle are innervating as a result of the step of applying the stimulation signal to the stimulation element may be accomplished in any number of suitable fashions, including but not limited to visual inspection of the muscle groups associated with a particular nerves, as well as the use of evoked muscle action potential (EMAP) monitoring techniques (that is, measuring the EMG responses of muscle groups associated with a particular nerve).

Although shown and described within the context of a particular exemplary system having a stimulation source and monitoring capacity, it will be appreciated by those skilled in the art that any number of systems for providing a stimulation signal and for monitoring to assess pedicle breach may be employed without departing from the scope of the present invention.

In a further aspect of the present invention, information relating to the step of assessing whether nerves adjacent the pedicle are innervating as a result of the step of applying the stimulation signal to the stimulation element may be communicated to the user. This information may include, but is not necessarily limited to, visual representations of the actual stimulation threshold of an exiting nerve root alone or in combination with the stimulation threshold of a bare nerve root (with or without the difference therebetween), as well as color coded graphics to indicate general ranges of pedicle integrity (i.e. "green" for a range of stimulation thresholds above a predetermined safe value—indicating "breach unlikely", "red" for range of stimulation thresholds below a predetermined unsafe value—indicating "breach likely", and "yellow" for the range of stimulation thresholds between the predetermined safe and unsafe values—indicating "possible breach"). This is a significant feature, and advantage over the prior art, in that it provides a straightforward and easy to interpret representation as to whether a pedicle has been breached, cracked, or otherwise compromised due to the formation and/or preparation of the pilot hole and/or due to the introduction of the pedicle screw into the pilot hole.

Identifying such a potential breach is helpful in that it prevents or minimizes the chance that a misplaced pedicle screw (that is, one breaching a wall of the pedicle) will be missed until after the surgery. Instead, any such misplaced pedicle screws, when stimulated according to the present invention, will produce an EMG response at a myotome level associated with the nerve in close proximity to the pedicle screw that is breaching the pedicle wall. This will indicate to the surgeon that the pedicle screw needs to be repositioned.

Figure 2:
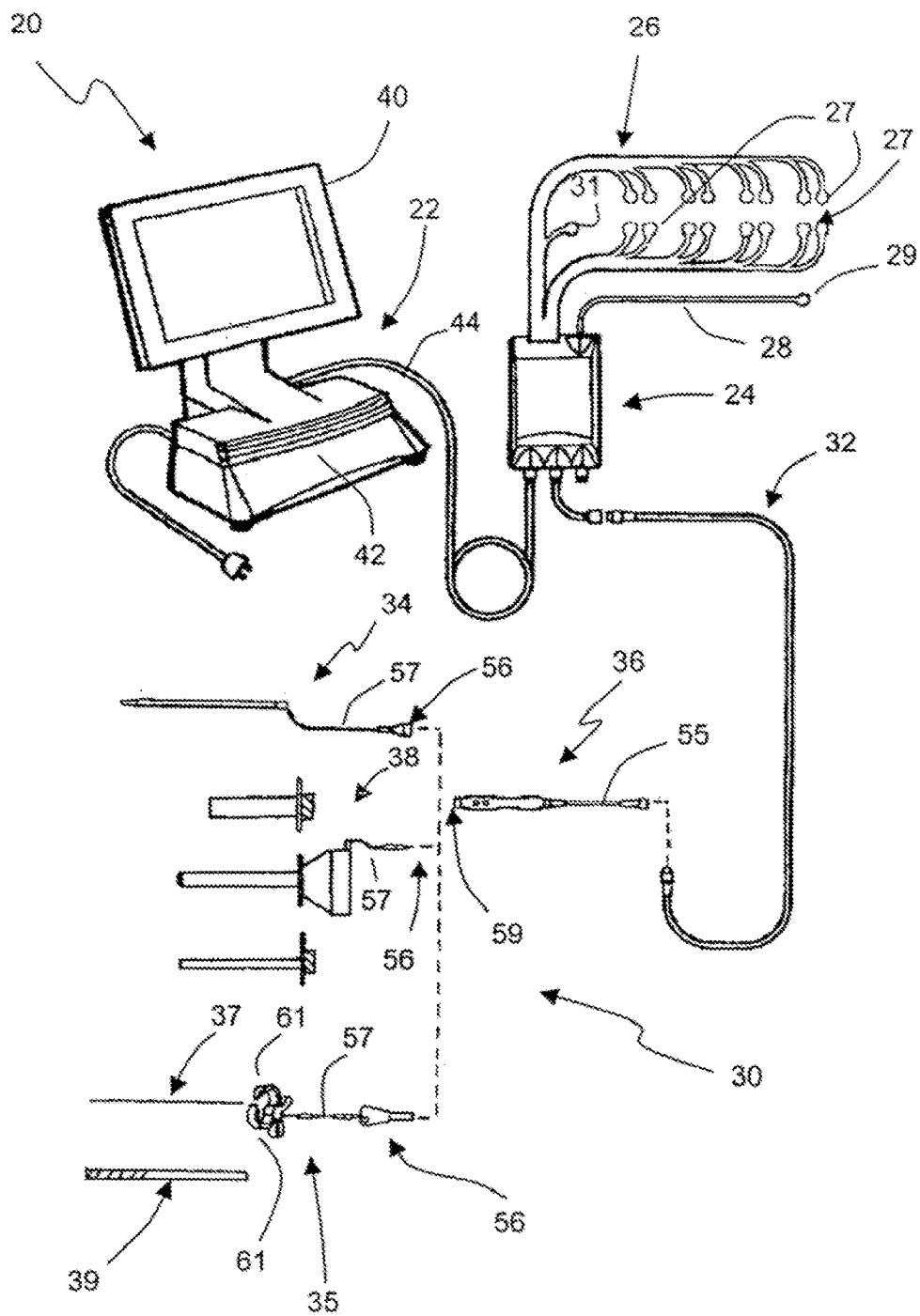
FIG. 2 is a perspective view of an exemplary surgical system 20 capable of assessing pedicle integrity according to the present invention.
Figure 3:
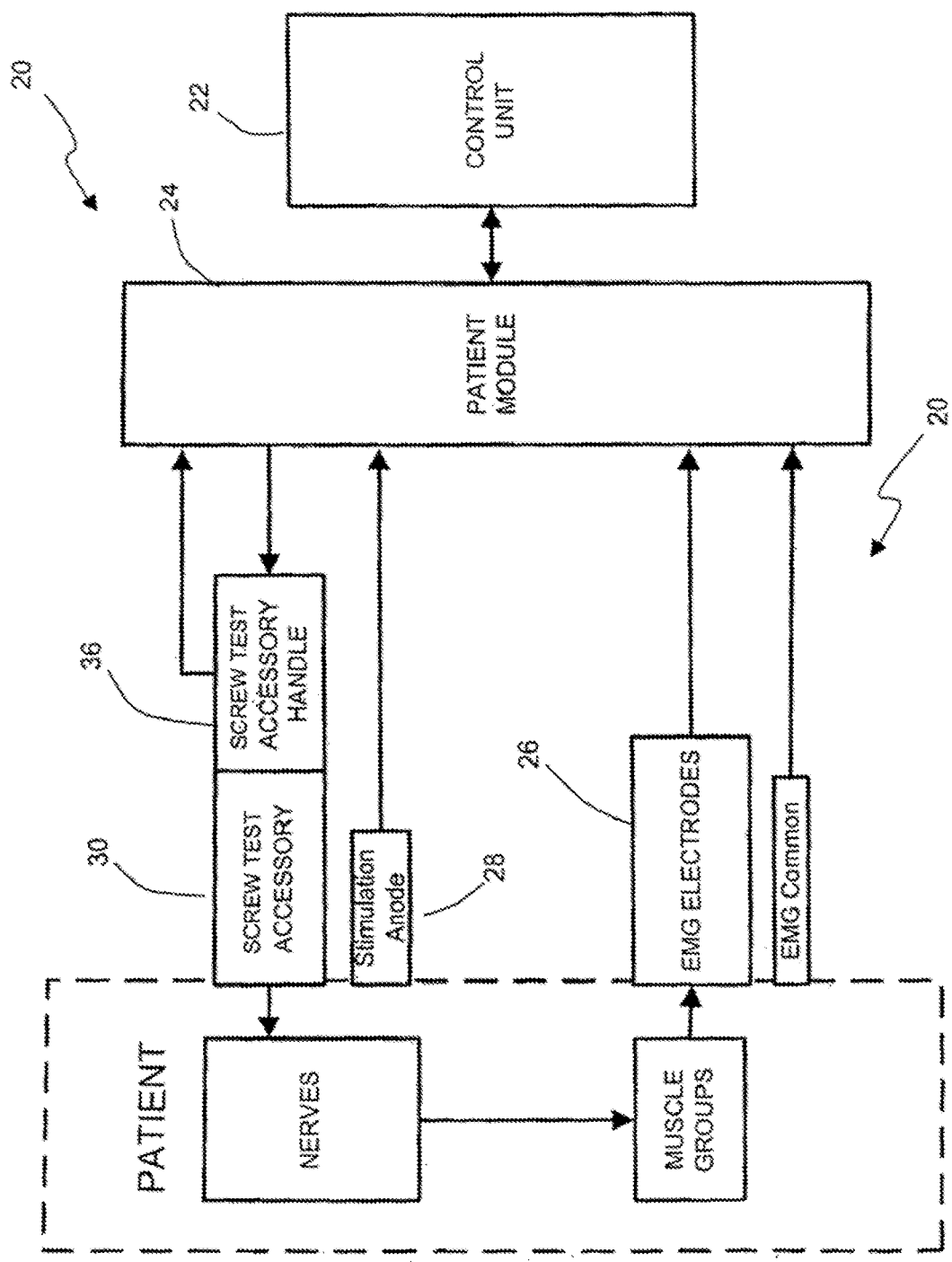
FIG. 3 is a block diagram of the surgical system 20 shown in FIG. 2.

FIGS. 2-3 illustrate, by way of example only, a surgical system 20 provided in accordance with a broad aspect of the present invention. The surgical system 20 includes a control unit 22, a patient module 24, an EMG harness 26 and return electrode 28 coupled to the patient module 24, and a host of pedicle screw test accessories 30 capable of being coupled to the patient module 24 via an accessory cable 32 in combination with a handle assembly 36. In the embodiment shown, the pedicle screw test accessories 30 include (by way of example only) a K-wire insulator 34, a universal insulating assembly 38, and a clamping-style electrical coupler 35. As will be described in greater detail below, a K-wire 37 and a tap member 39 are shown, by way of example, as exemplary stimulation elements according to the present invention. The K-wire 37 may be electrically coupled to the control unit 22 and/or patient module 24 (so as to receive a stimulation signal) through the use of the K-wire insulator 34, the universal insulating assembly 38 and/or the electrical coupler 35 (provided the K-wire 37 is insulated in some manner). The tap member 39 may be electrically coupled to the control unit 22 and/or patient module 24 (so as to receive a stimulation signal) through the use of the universal insulating assembly 38, the electrical coupler 35 (provided the tap member 39 is insulated in some manner) and/or by bringing a stimulation element into contact with the tap member 39, such as by (for example) providing a longitudinal cannulation within the tap member 39 and disposing an electrically coupled K-wire 37 therein.

The control unit 22 includes a touch screen display 40 and a base 42, which collectively contain the essential processing capabilities for controlling the surgical system 20. The patient module 24 is connected to the control unit 22 via a data cable 44, which establishes the electrical connections and communications (digital and/or analog) between the control unit 22 and patient module 24. The main functions of the control unit 22 include receiving user commands via the touch screen display 40, activating stimulation, processing signal data according to defined algorithms (described below), displaying received parameters and processed data, and monitoring system status and reporting fault conditions. The touch screen display 40 is preferably equipped with a graphical user interface (GUI) capable of communicating information to the user and receiving instructions from the user. The display 40 and/or base 42 may contain patient module interface circuitry that commands the stimulation sources, receives digitized signals and other information from the patient module 24, processes the EMG responses to extract characteristic information for each muscle group, and displays the processed data to the operator via the display 40.

As will be described in greater detail below, the surgical system 20 is capable of performing pedicle integrity assessments after the formation of the pilot hole, after preparation of the pilot hole, and/or after pedicle screw placement. Surgical system 20 accomplishes this by having the control unit 22 and patient module 24 cooperate to send stimulation signals to one or more stimulation electrodes or electrode regions on the various pedicle screw test accessories 30. Depending upon effect of pilot hole formation, pilot hole preparation and/or pedicle screw introduction (namely, on the bone forming the pedicle), the stimulation signals may cause nerves adjacent to or in the general proximity of the K-wire 37 and/or tap member 39 to innervate, which, in turn, can be monitored via the EMG harness 26. The pedicle integrity assessment feature of the present invention are based on assessing the evoked response of the various muscle myotomes monitored by the surgical system 20 via EMG harness 26.

The accessory handle assembly 36 includes a cable 55 for establishing electrical communication with the patient module 24 (via the accessory cable 32). In a preferred embodiment, each pedicle screw test accessory 30 (namely, K-wire insulator 34, universal insulating assembly 38, and electrical coupler 35) includes a proximal electrical connector 56, a distal electrical connector (described below), and an electrical cable 57 extending therebetween. The proximal electrical connector 56 is preferably threaded and designed to engage with the distal end 59 of the handle assembly 36. In this fashion, the screw test accessories 30 may be quickly and easily coupled (electrically and mechanically) to the accessory handle assembly 36. The distal electrical connector of the K-wire insulator 34 and universal insulating assembly 38 may comprise any number of suitable mechanisms for establishing electrical communication with an instrument passing therethrough (such as a K-wire 37 passing through the K-wire insulator 34 and/or the universal insulating assembly 38, and such as a tap member 39 extending through the universal insulating assembly 38). In a preferred embodiment, the distal electrical connectors within the universal insulating assembly 38 will be capable of expanding, moving or otherwise accommodating instruments of varying diameters according to the present invention. The distal electrical connector of the coupler 35 may include any number of suitable electrode or electrode regions (including protrusions) on or about the distal (or pinching) ends of the clamp arms 61 forming the coupler 35. Corresponding regions (such as electrodes or electrode regions—including indentations) may be provided on the K-wire 37, the tap member 39, such as where such devices are to be directly coupled to the handle assembly 36 (i.e. where K-wire 37 and/or tap member 39 are disposed through insulating elements that do not include distal electrical connectors) according to the present invention.

In all situations, the user may operate one or more buttons of the handle assembly 36 to selectively initiate a stimulation signal (preferably, a current signal) from the patient module 24 to the pedicle probe 56. With the K-wire 37 and/or tap member 39 touching the interior wall of the fully formed pilot hole and/or the K-wire 37 touching the fully introduced pedicle screw, applying a stimulation signal in this fashion serves to test the integrity of the medial wall of the pedicle. That is, a breach or compromise in the integrity of the pedicle will allow the stimulation signal to pass through the pedicle and innervate an adjacent nerve root. By monitoring the myotomes associated with the nerve roots (via the EMG harness 26 and recording electrode 27) and assessing the resulting EMG responses (via the control unit 22), the surgical system 20 can assess whether a pedicle breach occurred during hole formation and/or screw introduction. If a breach or potential breach is detected, the user may simply withdraw the misplaced pedicle screw and redirect to ensure proper placement.

Figure 4:
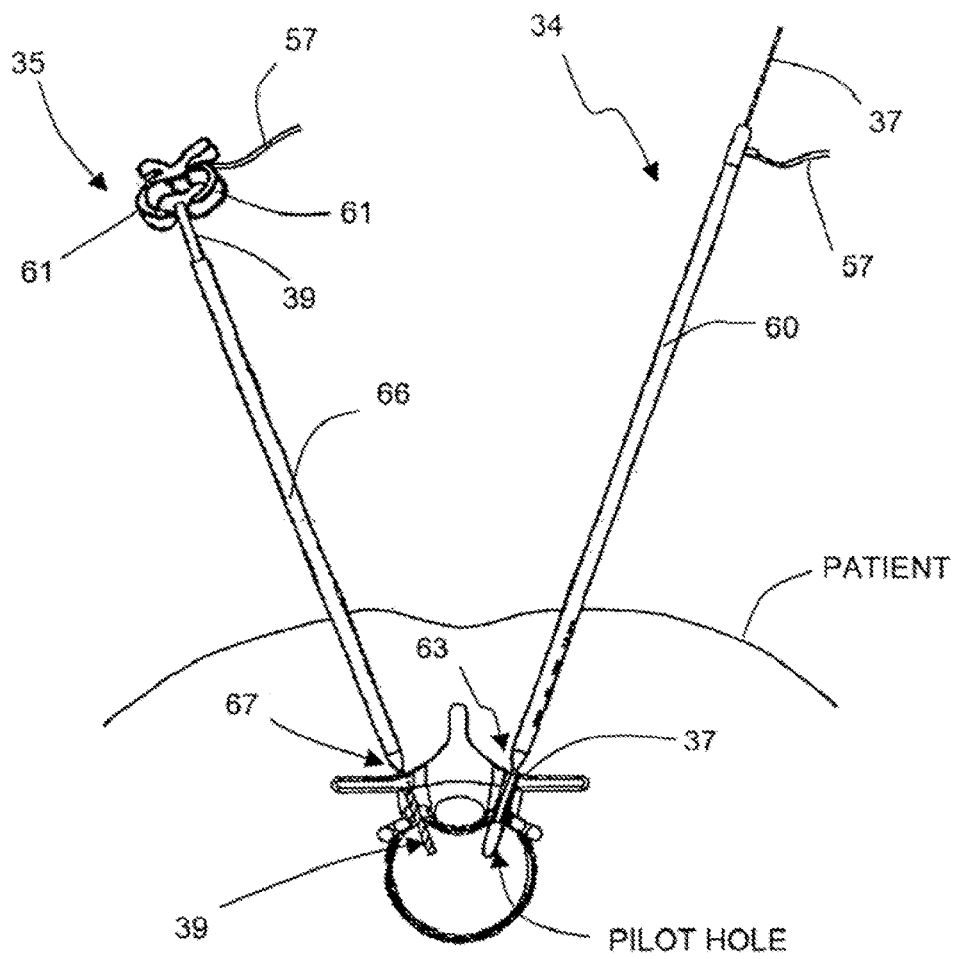
FIG. 4 is a side view illustrating the use of first and second exemplary systems for assessing pedicle integrity according to the present invention.
Figure 6:
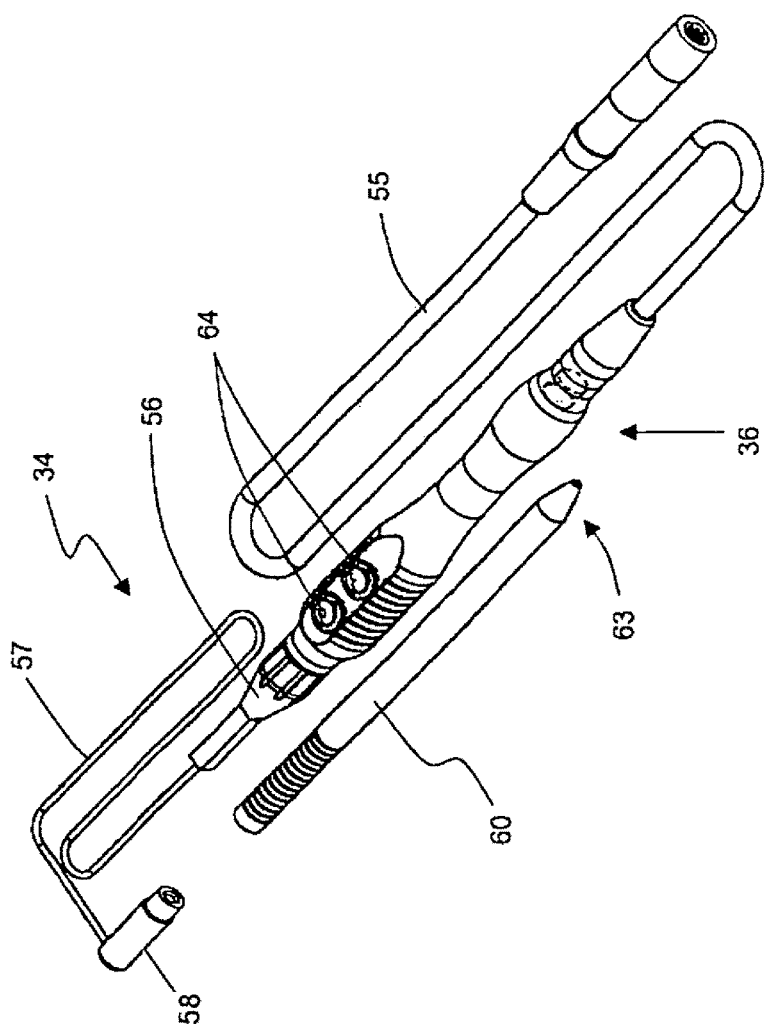
FIG. 6 is a perspective view of the first exemplary system for assessing pedicle integrity according to the present invention, comprising a K-wire insulator electrically coupled to a handle assembly.

FIG. 4 illustrates two exemplary manners of performing pedicle integrity assessments according to the present invention, one employing the K-wire insulator 34 and one employing the electrical coupler 35. With combined reference with FIG. 6, the K-wire insulator 34 according to the present invention includes an elongate insulating body 60 having a tapered distal end 63, open distal and proximal ends, and a lumen or cannulation extending therebetween dimensioned to receive and pass the K-wire 37. A cap element 58 is provided for placement in the proximal end of the insulating body 60. The cap element 58 has a lumen therewithin dimensioned to pass the K-wire 37 and includes the distal electrical connector (not shown) coupled to the electrical cable 57. As shown in FIG. 4, the K-wire insulator 34 may be advanced to the pedicle target site in a percutaneous fashion, by either establishing a virgin approach to the pedicle target site or by passing through a previously established percutaneous corridor (such as may be left or formed by commercially available percutaneous pedicle screw placement systems). This process may be facilitated by first establishing a pilot hole through the use of a so-called Jam-Sheede needle (comprising an inner rigid needle element disposed within a rigid outer needle element), after which point the inner rigid needle element is removed such that the K-wire 37 may be introduced into the pilot hole. The outer rigid needle element of the Jam-Sheede device may then be removed, leaving the K-wire 37 in place. The K-wire insulator 34 may then be advanced over the K-wire 37. Once the distal end 63 of the K-wire insulator 34 abuts the opening of the pedicle pilot hole, buttons 64 on the handle member 36 may be employed to apply the stimulation signal to the K-wire 37. In this fashion, the majority of the K-wire 37 is insulated from the surrounding tissue, while the distal end of the K-wire 37 may be brought into direct contact with the pilot hole to perform pedicle integrity assessments according to one embodiment of the present invention. As will be appreciated, this same technique could be employed to bring the stimulation electrode or electrode region of the K-wire 37 into contact with a portion of a fully inserted pedicle screw (not shown).

FIG. 4 also illustrates that the electrical coupler 35 may be employed to perform pedicle integrity assessments, by way of example only, by establishing electrical communication between the fully inserted tap member 39 and the interior surface of the now-prepared pilot hole. The electrical coupler 35 accomplishes this by engaging the electrode or electrode regions on the opposing clamping arms 61 against a portion of the proximal end of the tap member 39. To facilitate this, the tap member 39 may be equipped with indentations or similar features for matingly engaging with corresponding features on the distal regions of the clamping arms 61. In the embodiment shown, an insulated cannula 66 is provided for insulating all but the exposed distal and proximal ends of the tap member 39. As with the body 60 of the K-wire insulator 34, the insulated cannula 66 is preferably equipped with a tapered distal end 67. In use, the tap member 39 will be advanced through the insulated cannula 66 (such as by being passed over a K-wire 37 via an internal cannulation) and rotated to prepare threads along the interior of the pilot hole. After the pilot hole has been fully prepared in this fashion (that is, to the full or approximately full depth of the pilot hole), the handle member 36 may be used to apply the stimulation signal to the electrical coupler 35 which, in turn, transmits this stimulation signal to the interior of the prepared pilot hole to perform pedicle integrity assessments according to another embodiment of the present invention. If the pedicle has not been breached, the tap member 39 may then be removed and a pedicle screw introduced into the prepared pilot hole. By selecting a pedicle screw having the same approximate characteristics (i.e. pitch, thread height, diameter, length, etc . . . ) as the tapping (distal) portion of the tap member 39, the need to perform further pedicle integrity assessments after full introduction of the pedicle screw may be obviated.

Figure 5:
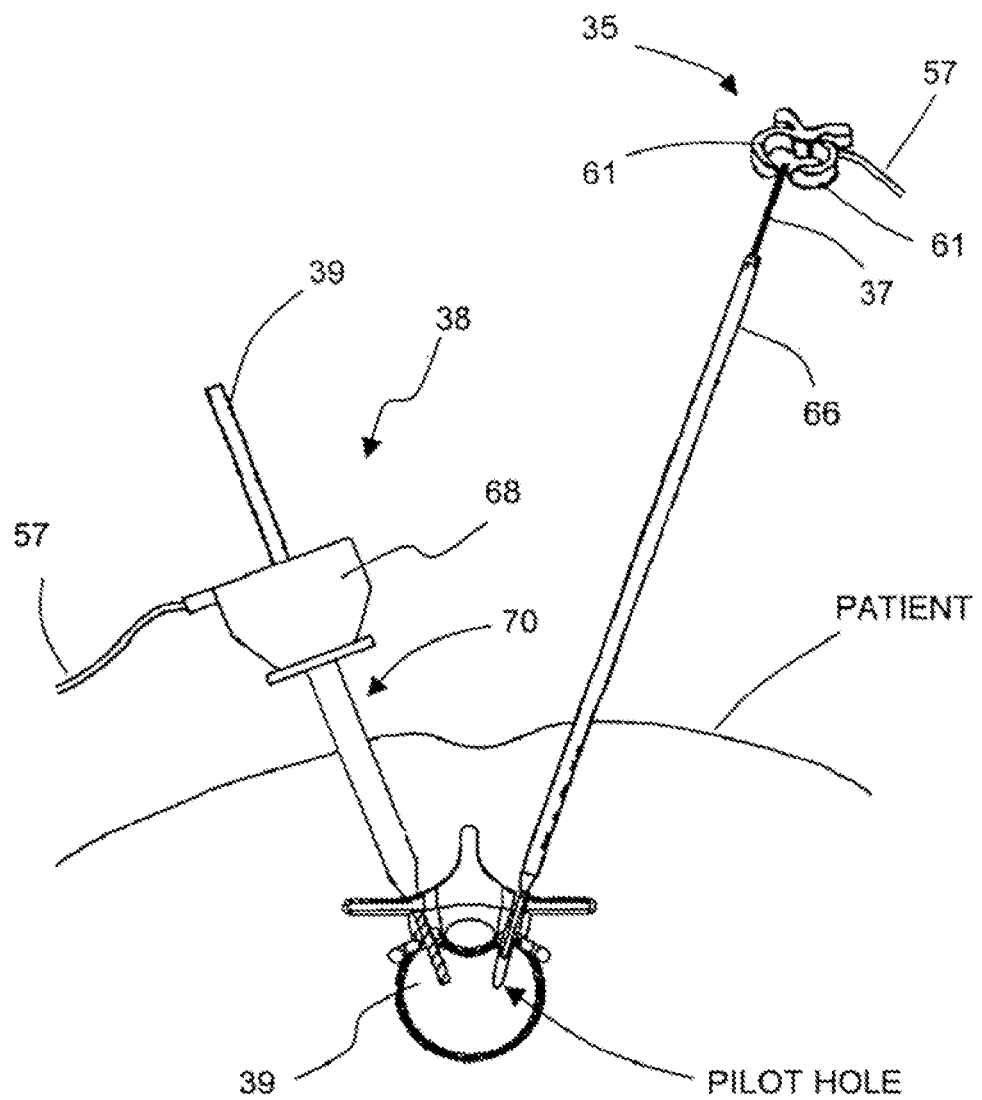
FIG. 5 is a side view illustrating the use of third and fourth exemplary systems for assessing pedicle integrity according to the present invention.
Figure 7:
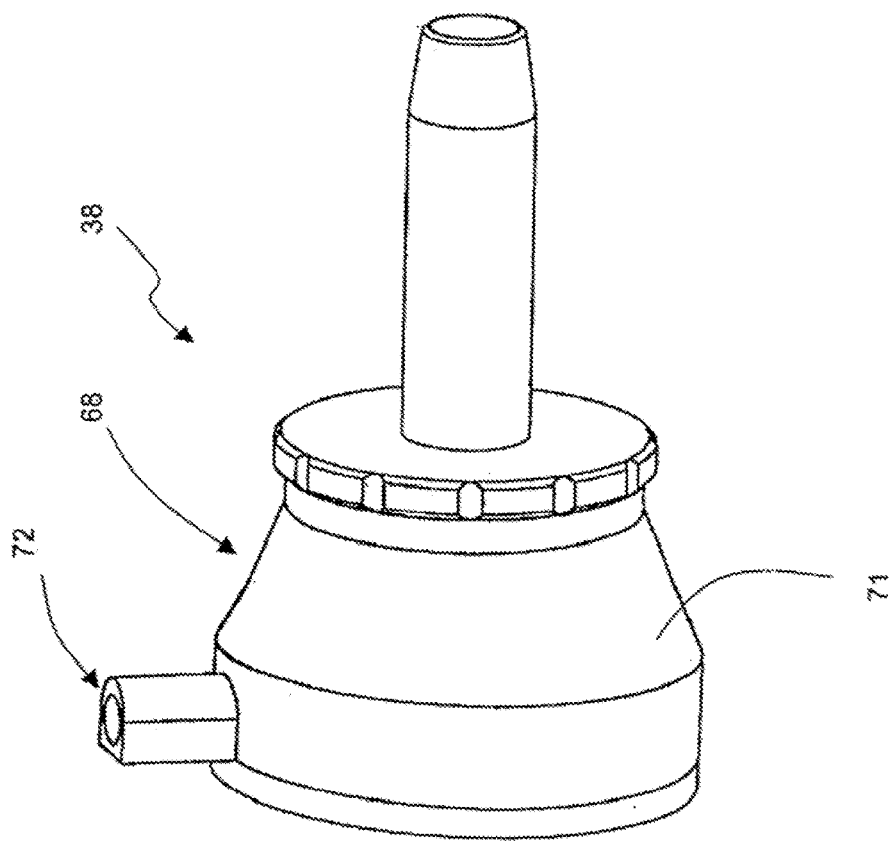
FIG. 7 is a perspective view of the third exemplary system for assessing pedicle integrity according to the present invention, comprising a universal insulating assembly including a handle assembly coupled to an insulating cannula according to the present invention.
Figure 8:
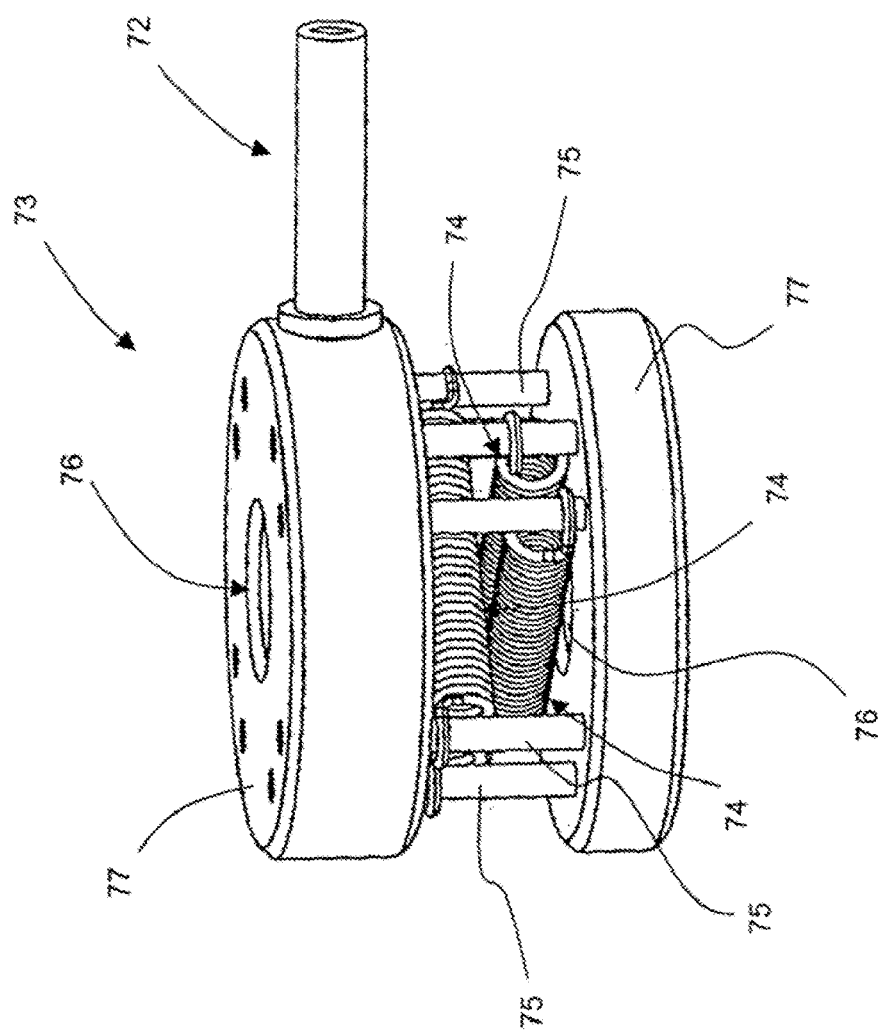
FIG. 8 is a perspective view illustrating an exemplary electrical coupling mechanism capable of being disposed within the handle assembly shown in FIG. 7.
Figure 9:
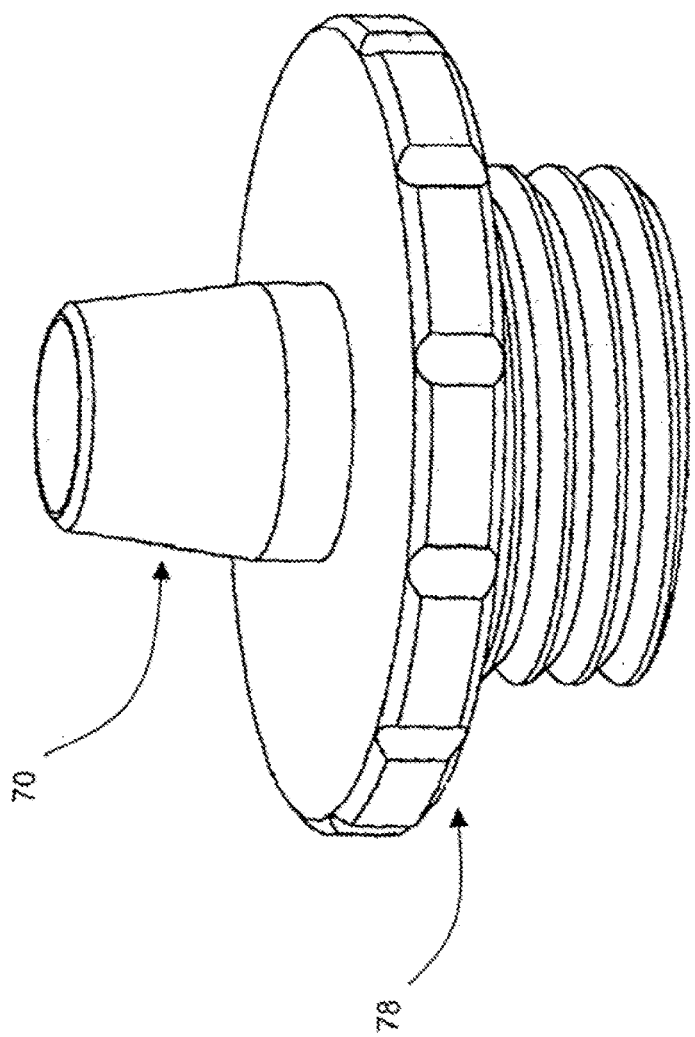
FIGS. 9-11 are perspective views illustrating insulating cannulas of varying sizes and dimensions for use with the handle assembly according to the present invention.
Figure 10:
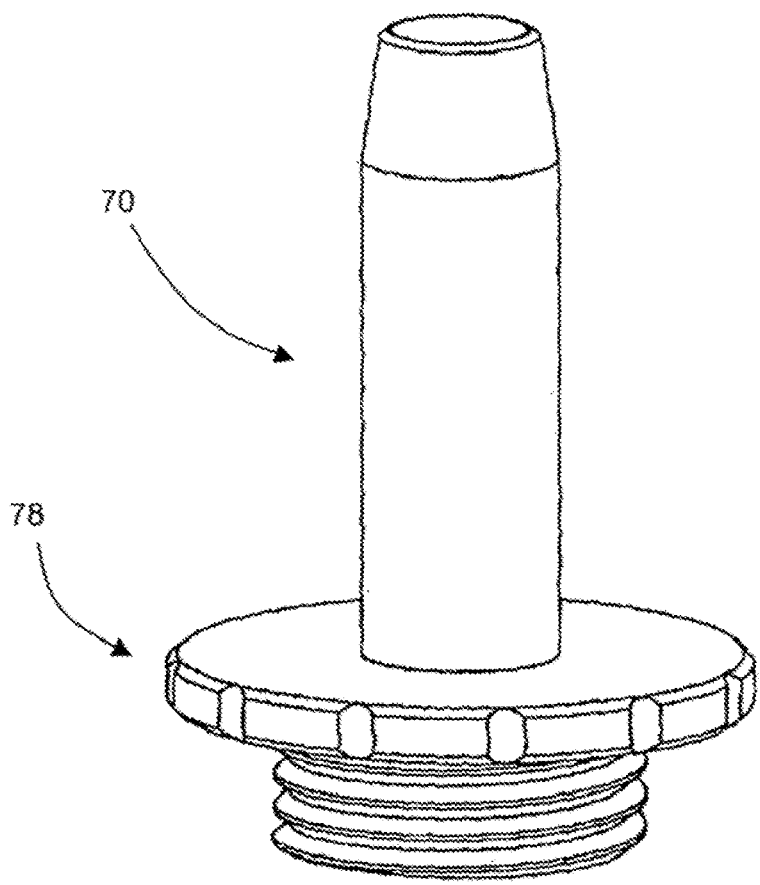
Figure 11:
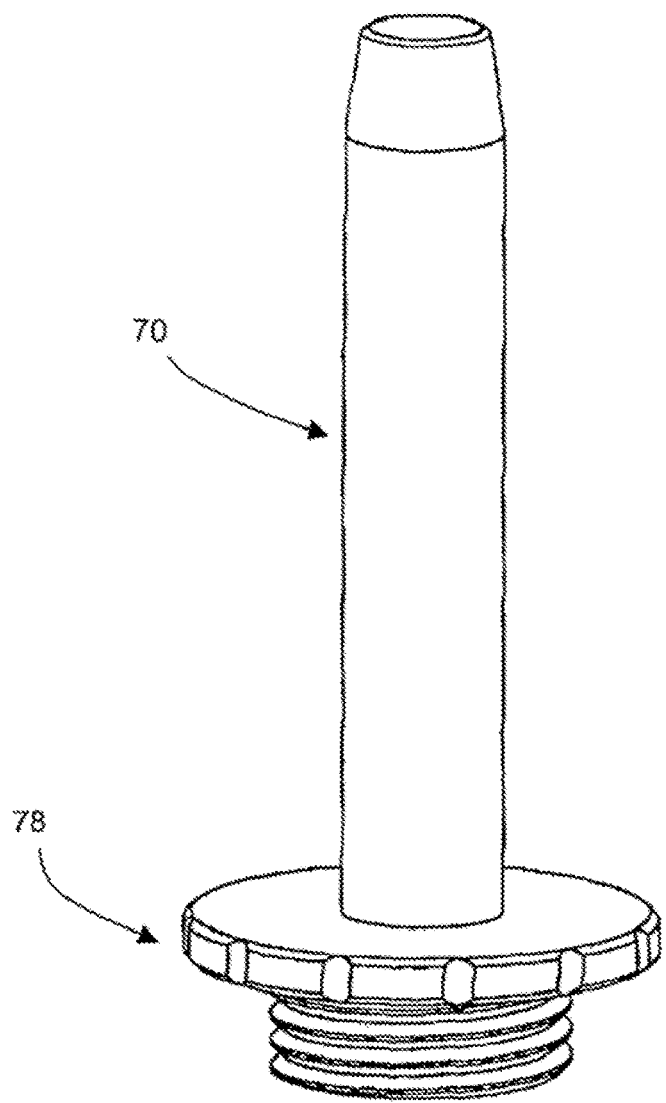

FIG. 5 illustrates two more exemplary manners of performing pedicle integrity assessments according to the present invention, one employing the universal insulating assembly 38 and one employing the electrical coupler 35. With combined reference to FIGS. 7-11, the universal insulating assembly 38 includes a handle assembly 68 and an insulated cannula 70 extending from the distal portion of the handle assembly 68. As best seen in FIG. 7, the handle assembly 68 includes a housing member 71 and an electrical connector port 72 for connection with the electrical cable 57. With reference to FIG. 8, the housing member 71 contains a universal electrical coupling mechanism 73 comprising, by way of example, a plurality of contact elements 74 (in this case springs extending between posts 75). A lumen 76 is provided (by way of example only) in the approximate center of (and extending between) upper and lower base members 77. The contact elements 74 are positioned in a transverse fashion such that they intersect generally in the same plane as the center of the lumen 76. In this fashion, any metallic or conductive instrument passed through the lumen 76 will be brought into contact with the contact elements 74, thereby providing the ability to apply an electrical signal to the instrument. Moreover, the contact elements 74 are capable of moving, expanding, or otherwise accommodating instruments having a variety of diameters. As best shown in FIGS. 9-11, the insulated cannula 70 may be provided having any number of different lengths and widths, depending upon the device to be passed through it. A threaded base member 78 is preferably coupled to each insulated cannula 70 to facilitate coupling the particular insulated cannula 70 to a corresponding threaded portion on the distal region of the housing member 71. In this fashion, a surgeon may quickly and easily change between any of a variety of insulating cannulas 70 depending upon the application (i.e. depth to the pedicle target site) and the device to be passed therethrough (i.e. the tap member 39 as shown in FIG. 5).

The insulating cannula 70 serves to isolate a portion of the instrument as it is passed through the handle assembly 68. In this fashion, the insulating cannula 70 may be advanced to a pedicle target site, such as to the opening of a pedicle pilot hole as shown in FIG. 5. Although not shown, it is to be readily appreciated that the present invention also contemplates advancing the distal end of the insulating cannula 70 over or in general abutment with a proximal portion of a percutaneously placed pedicle screw) pedicle screw. In either instance, an instrument or device (such as, by way of example, K-wire 37 or the tap member 39, depending upon the situation) may be passed through the handle member 68 until the tip of the instrument reaches either the initially formed pilot hole, the fully prepared pilot hole, and/or the fully introduced pedicle screw. The insulating cannulas 70 are of varying size depending upon the particular target site and surgical application, but may preferably be provided ranging from 0 inches to 24 inches in length and of any diameter suitable to pass the instrument of interest.

FIG. 5 also illustrates a variant of the embodiment shown in FIG. 4, except that the insulated cannula 66 is specifically dimensioned to pass the K-wire 37, as opposed to larger diameter instruments such as the tap member 39 as shown in FIG. 4. In this instance, the electrical coupler 35 may be used to establish electrical communication between the K-wire 37 and the interior of a pilot hole. With the distal end of the K-wire 37 in such electrical communication with the interior of the pilot hole, the handle assembly 36 may be employed to apply the stimulation signal to perform a pedicle integrity assessment according to the present invention. Placement of the K-wire 37 within the pilot hole, and the advancement of the insulated cannula 66, may be the same as described above with reference to the Jam-Sheede device described above.

As noted above, the system 20 described generally above is exemplary of a system including a stimulation source and monitoring capacity for use in performing pedicle integrity assessment according to the present invention. It will be appreciated by those skilled in the art, however, that any number of systems for providing a stimulation signal and for monitoring to assess pedicle breach may be employed without departing from the scope of the present invention. That said, the following discussion elaborates on the particular algorithms and principles behind the neurophysiology for performing pedicle integrity assessments according to the exemplary embodiment shown (system 20 of FIGS. 2-3) according to the present invention.

Figure 13:
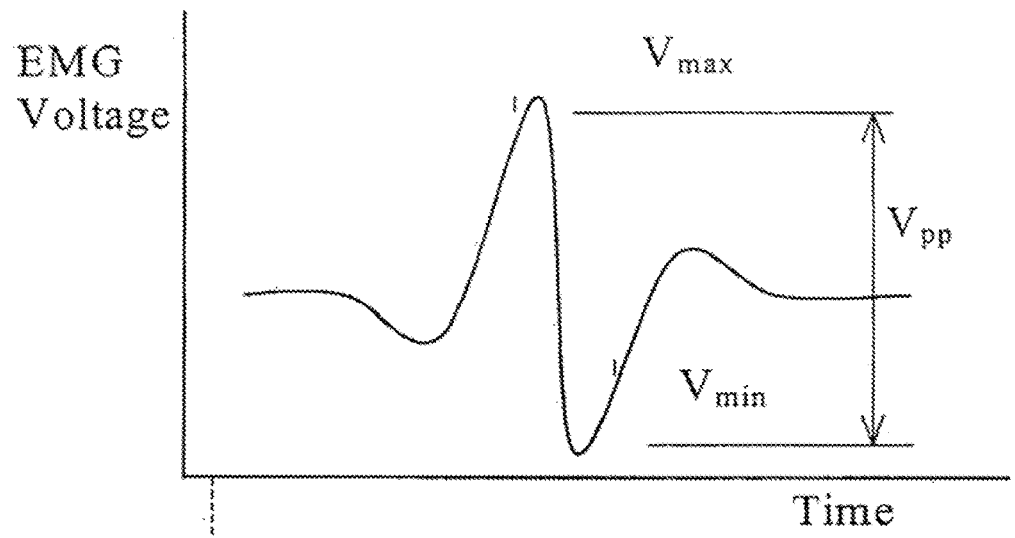
FIG. 13 is a graph illustrating a plot of the neuromuscular response (EMG) of a given myotome over time based on a current stimulation pulse (such as shown in FIG. 12) applied to a nerve bundle coupled to the given myotome.
Figure 12:
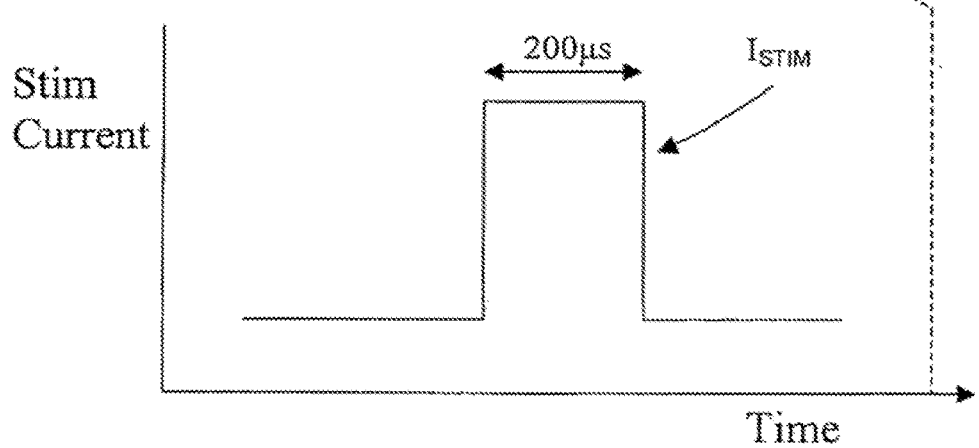
FIG. 12 is a graph illustrating a plot of a stimulation current pulse capable of producing a neuromuscular response (EMG) of the type shown in FIG. 13.

FIGS. 12 and 13 illustrate a fundamental aspect of the present invention: a stimulation signal (FIG. 12) and a resulting evoked response (FIG. 13). By way of example only, the stimulation signal is preferably a stimulation current signal ($I_{Stim}$) having rectangular monophasic pulses with a frequency and amplitude adjusted by system software. In a still further preferred embodiment, the stimulation current ($I_{Stim}$) may be coupled in any suitable fashion (i.e. AC or DC) and comprises rectangular monophasic pulses of 200 microsecond duration. The amplitude of the current pulses may be fixed, but will preferably sweep from current amplitudes of any suitable range, such as from 2 to 100 mA. For each nerve and myotome there is a characteristic delay from the stimulation current pulse to the EMG response (typically between 5 to 20 ms). To account for this, the frequency of the current pulses is set at a suitable level such as, in a preferred embodiment, 4 Hz to 10 Hz (and most preferably 4.5 Hz), so as to prevent stimulating the nerve before it has a chance to recover from depolarization. The EMG response shown in FIG. 13 can be characterized by a peak-to-peak voltage of $V_{pp}=V_{max}-V_{min}$.

Figure 14:
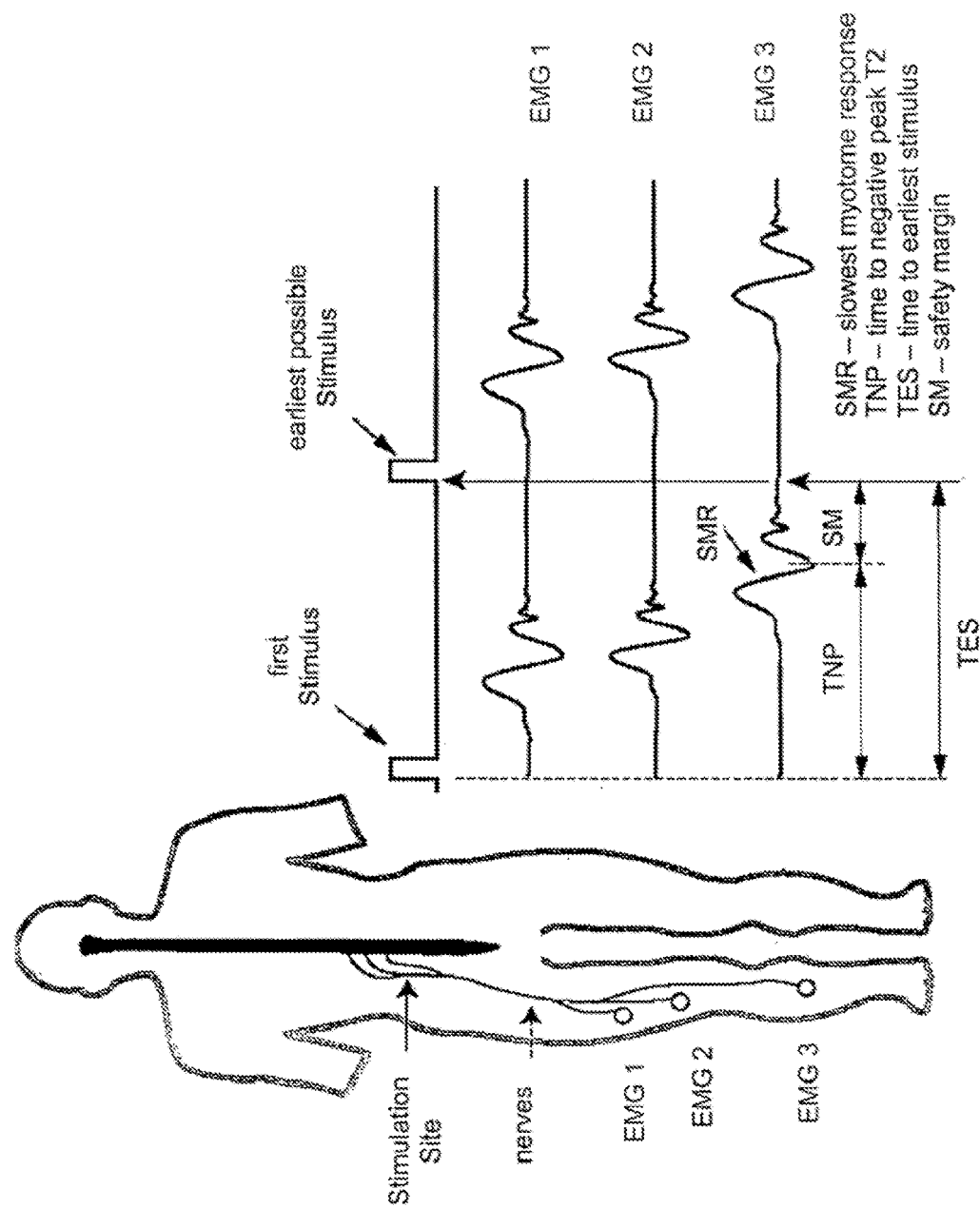
FIG. 14 is an illustrating (graphical and schematic) of a method of automatically determining the maximum frequency ($F_{Max}$) of the stimulation current pulses according to one embodiment of the present invention.

FIG. 14 illustrates an alternate manner of setting the maximum stimulation frequency, to the extent it is desired to do so rather than simply selecting a fixed maximum stimulation frequency (such as 4.5 Hz) as described above. According to this embodiment, the maximum frequency of the stimulation pulses is automatically adjusted. After each stimulation, Fmax will be computed as: $Fmax=1/(T2+T_{Safety\ Margin})$ for the largest value of T2 from each of the active EMG channels. In one embodiment, the Safety Margin is 5 ms, although it is contemplated that this could be varied according to any number of suitable durations. Before the specified number of stimulations, the stimulations will be performed at intervals of 100-120 ms during the bracketing state, intervals of 200-240 ms during the bisection state, and intervals of 400-480 ms during the monitoring state. After the specified number of stimulations, the stimulations will be performed at the fastest interval practical (but no faster than Fmax) during the bracketing state, the fastest interval practical (but no faster than Fmax/2) during the bisection state, and the fastest interval practical (but no faster than Fmax/4) during the monitoring state. The maximum frequency used until $F_{max}$ is calculated is preferably 10 Hz, although slower stimulation frequencies may be used during some acquisition algorithms. The value of $F_{max}$ used is periodically updated to ensure that it is still appropriate. For physiological reasons, the maximum frequency for stimulation will be set on a per-patient basis. Readings will be taken from all myotomes and the one with the slowest frequency (highest T2) will be recorded.

Figure 15:
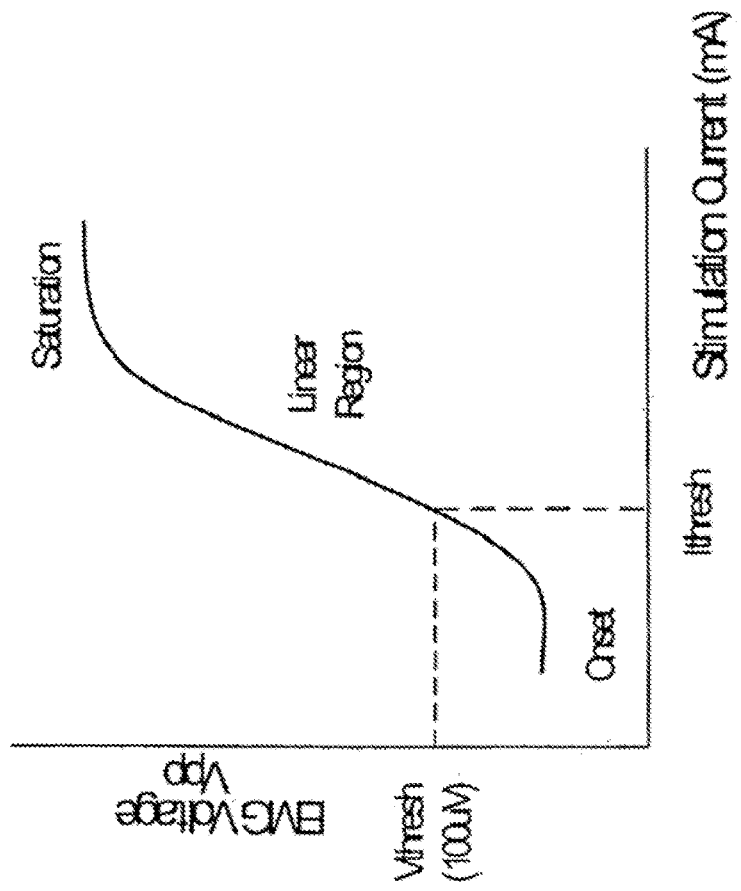
FIG. 15 is a graph illustrating a plot of EMG response peak-to-peak voltage (Vpp) for each given stimulation current level ($I_{Stim}$) forming a stimulation current pulse according to the present invention (otherwise known as a "recruitment curve")

A basic premise behind the neurophysiology employed in the present invention is that each nerve has a characteristic threshold current level ($I_{Thresh}$) at which it will depolarize. Below this threshold, current stimulation will not evoke a significant EMG response ($V_{pp}$). Once the stimulation threshold ($I_{Thresh}$) is reached, the evoked response is reproducible and increases with increasing stimulation until saturation is reached. This relationship between stimulation current and EMG response may be represented graphically via a so-called "recruitment curve," such as shown in FIG. 15, which includes an onset region, a linear region, and a saturation region. By way of example only, the present invention defines a significant EMG response to have a Vpp of approximately 100 uV. In a preferred embodiment, the lowest stimulation current that evokes this threshold voltage ($V_{Thresh}$) is called $I_{Thresh}$. As will be described in greater detail below, changes in the current threshold ($I_{Thresh}$) may be indicative of a change in the degree of electrical communication between a stimulation electrode and a nerve. This is helpful in assessing if a screw or similar instrument has inadvertently breached the cortex of a pedicle. More specifically, where an initial determination of ($I_{Thresh}$), such as by applying a stimulation current to the interior of a hole created to receive a pedicle screw, is greater than a later determination of ($I_{Thresh}$), such as by applying a stimulation current to the tip of the pedicle screw after insertion, the decrease in $I_{Thresh}$, if large enough, may indicate electrical communication between the pedicle screw and the nerve. Based on the insulation properties of bone, such electrical communication would indicate a breach of the pedicle.

Figure 16:
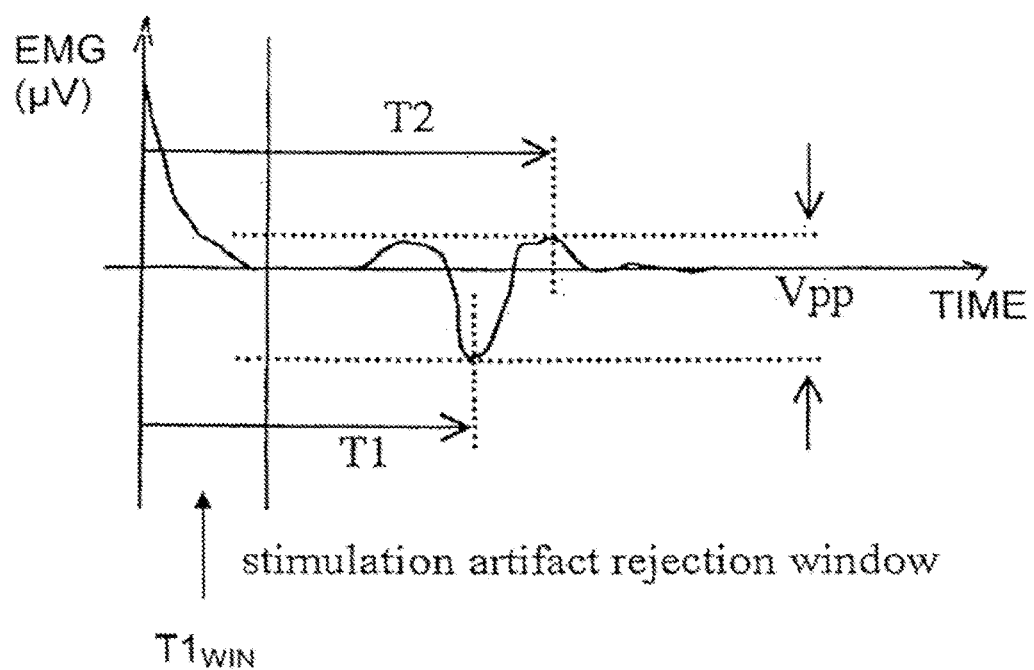
FIG. 16 is a graph illustrating a traditional stimulation artifact rejection technique as may be employed in obtaining each peak-to-peak voltage (Vpp) EMG response according to the present invention.
Figure 17:
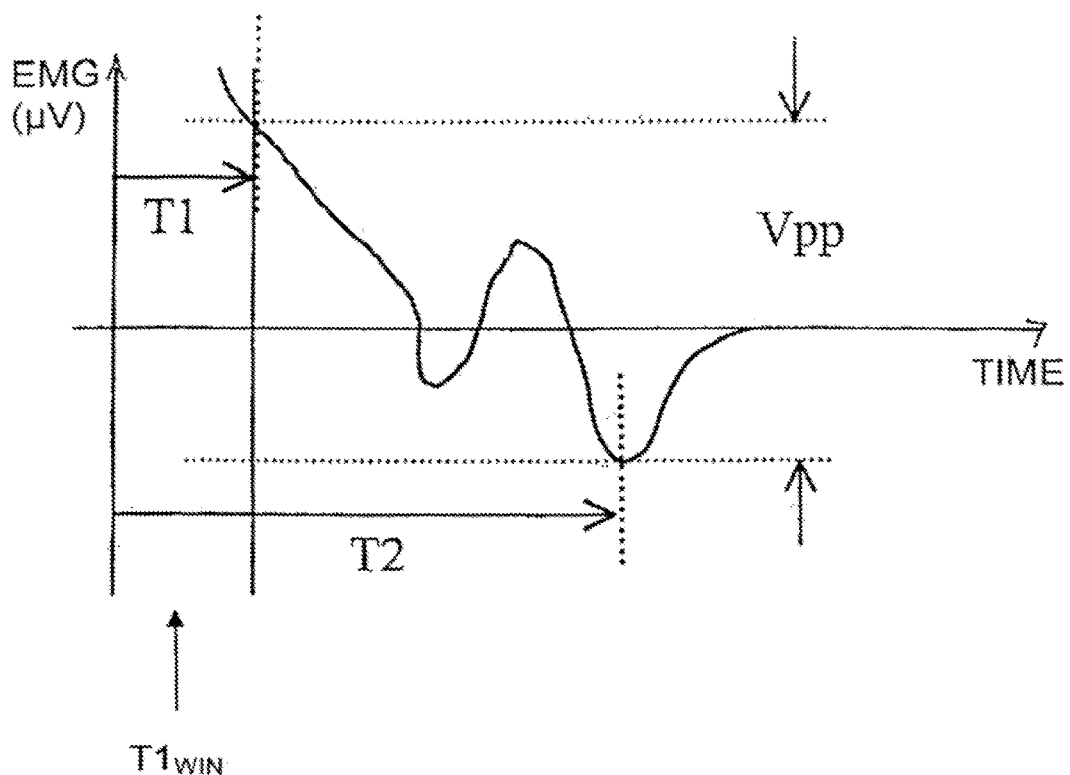
FIG. 17 is a graph illustrating the traditional stimulation artifact rejection technique of FIG. 16, wherein a large artifact rejection causes the EMG response to become compromised.

In order to obtain this useful information, the present invention must first identify the peak-to-peak voltage (Vpp) of each EMG response corresponding a given stimulation current ($I_{Stim}$). The existence stimulation and/or noise artifacts, however, can conspire to create an erroneous Vpp measurement of the electrically evoked EMG response. To overcome this challenge, the surgical system 20 of the present invention may employ any number of suitable artifact rejection techniques, including the traditional stimulation artifact rejection technique shown in FIG. 16. Under this technique, stimulation artifact rejection is undertaken by providing a simple artifact rejection window $T1_{WIN}$ at the beginning of the EMG waveform. During this T1 window, the EMG waveform is ignored and Vpp is calculated based on the max and min values outside this window. (T1 is the time of the first extremum (min or max) and T2 is the time of the second extremum.) In one embodiment, the artifact rejection window $T1_{WIN}$ may be set to about 7.3 msec. While generally suitable, there are situations where this stimulation artifact rejection technique of FIG. 16 is not optimum, such as in the presence of a large stimulation artifact (see FIG. 17). The presence of a large stimulation artifact causes the stimulation artifact to cross over the window $T1_{WIN}$ and blend in with the EMG. Making the stimulation artifact window larger is not effective, since there is no clear separation between EMG and stimulation artifact.

Figure 18:
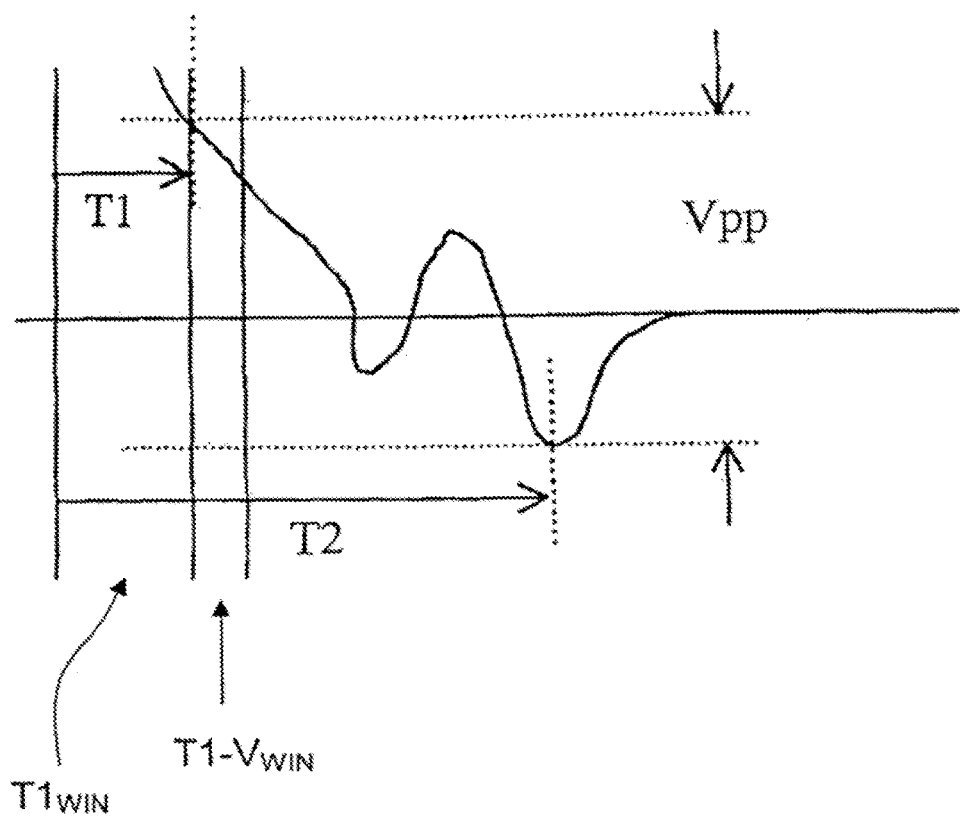
FIG. 18 is a graph illustrating an improved stimulation artifact rejection technique according to the present invention.

FIG. 18 illustrates a stimulation artifact rejection technique according to the present invention, which solves the above-identified problem with traditional stimulation artifact rejection. Under this technique, a T1 validation window ($T1-V_{WIN}$) is defined immediately following the T1 window ($T1_{WIN}$). If the determined Vpp exceeds the threshold for recruiting, but T1 falls within this T1 validation window, then the stimulation artifact is considered to be substantial and the EMG is considered to have not recruited. An operator may be alerted, based on the substantial nature of the stimulation artifact. This method of stimulation artifact rejection is thus able to identify situations where the stimulation artifact is large enough to cause the Vpp to exceed the recruit threshold. To account for noise, the T1 validation window ($T1-V_{WIN}$) should be within the range of 0.1 ms to 1 ms wide (preferably about 0.5 ms). The T1 validation window ($T1-V_{WIN}$) should not be so large that the T1 from an actual EMG waveform could fall within.

Figure 19:
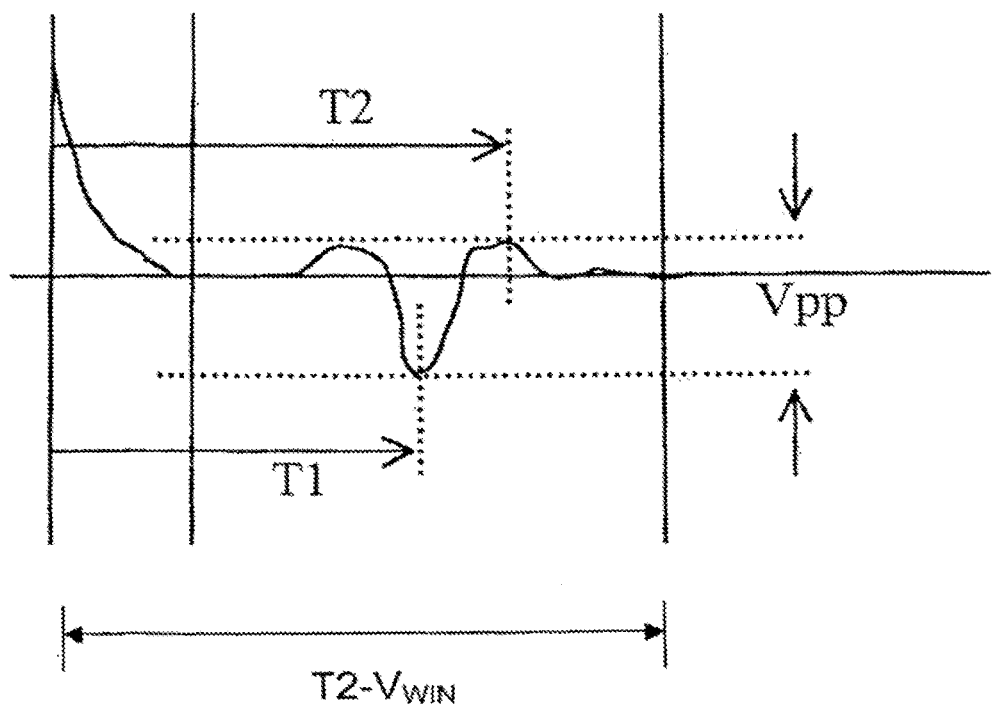
FIG. 19 is a graph illustrating an improved noise artifact rejection technique according to the present invention.

FIG. 19 illustrates a noise artifact rejection technique according to the present invention. When noise artifacts fall in the time window where an EMG response is expected, their presence can be difficult to identify. Artifacts outside the expected response window, however, are relatively easy to identify. The present invention capitalizes on this and defines a T2 validation window ($T2-V_{WIN}$) analogous to the T1 validation window ($T1-V_{WIN}$) described above with reference to FIG. 18. As shown, T2 must occur prior to a defined limit, which, according to one embodiment of the present invention, may be set having a range of between 40 ms to 50 ms (preferably about 47 ms). If the Vpp of the EMG response exceeds the threshold for recruiting, but T2 falls beyond the T2 validation window ($T2-V_{WIN}$), then the noise artifact is considered to be substantial and the EMG is considered to have not recruited. An operator may be alerted, based on the substantial nature of the noise artifact.

Figure 20:
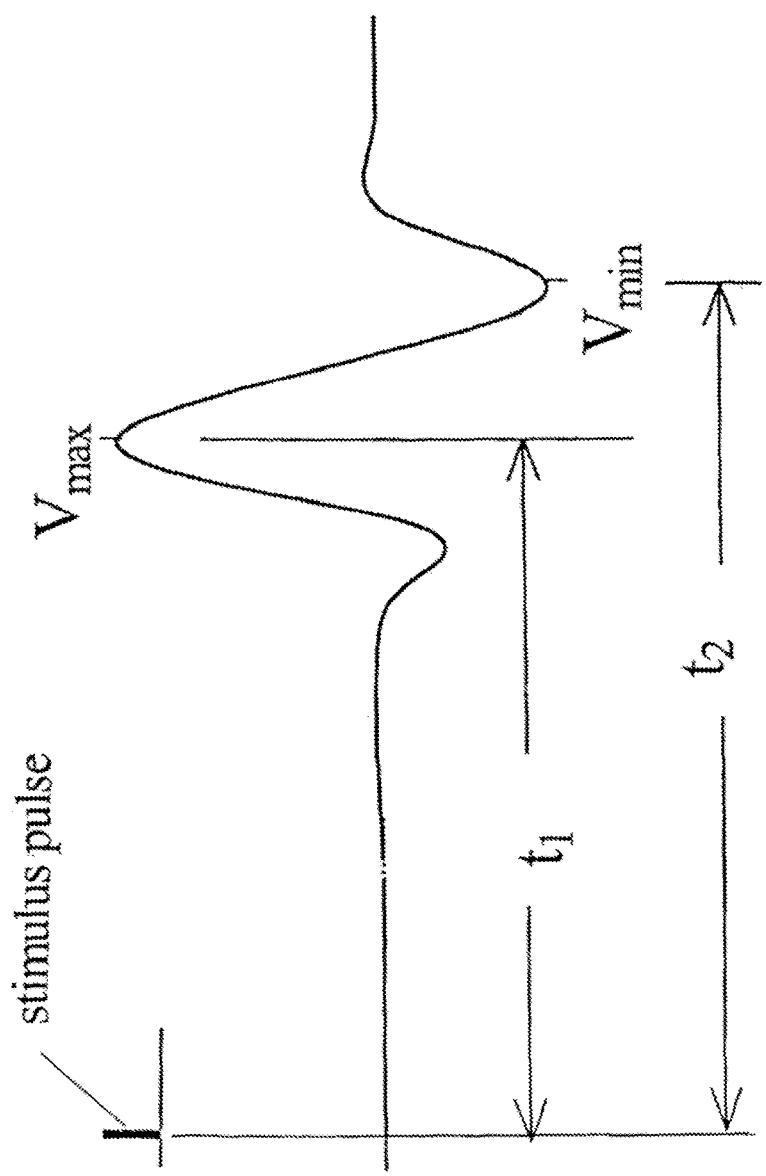
FIG. 20 is a graph illustrating a plot of a neuromuscular response (EMG) over time (in response to a stimulus current pulse) showing the manner in which voltage extrema ($V_{Max\ or\ Min}$), ($V_{Min\ or\ Max}$) occur at times T1 and T2, respectively.
Figure 21:
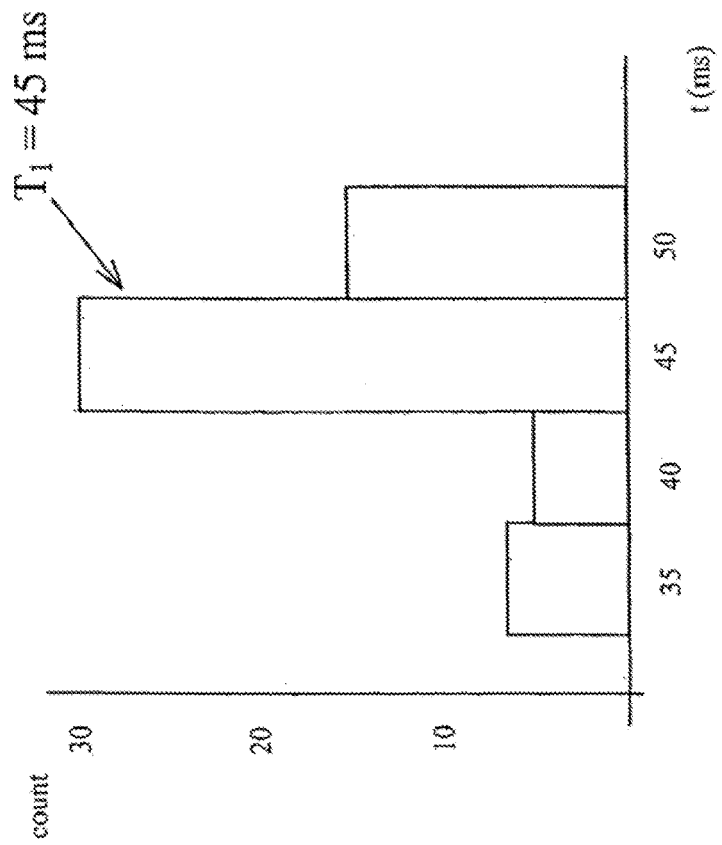
FIG. 21 is a graph illustrating a histogram as may be employed as part of a T1, T2 artifact rejection technique according to an alternate embodiment of the present invention.
Figure 23:
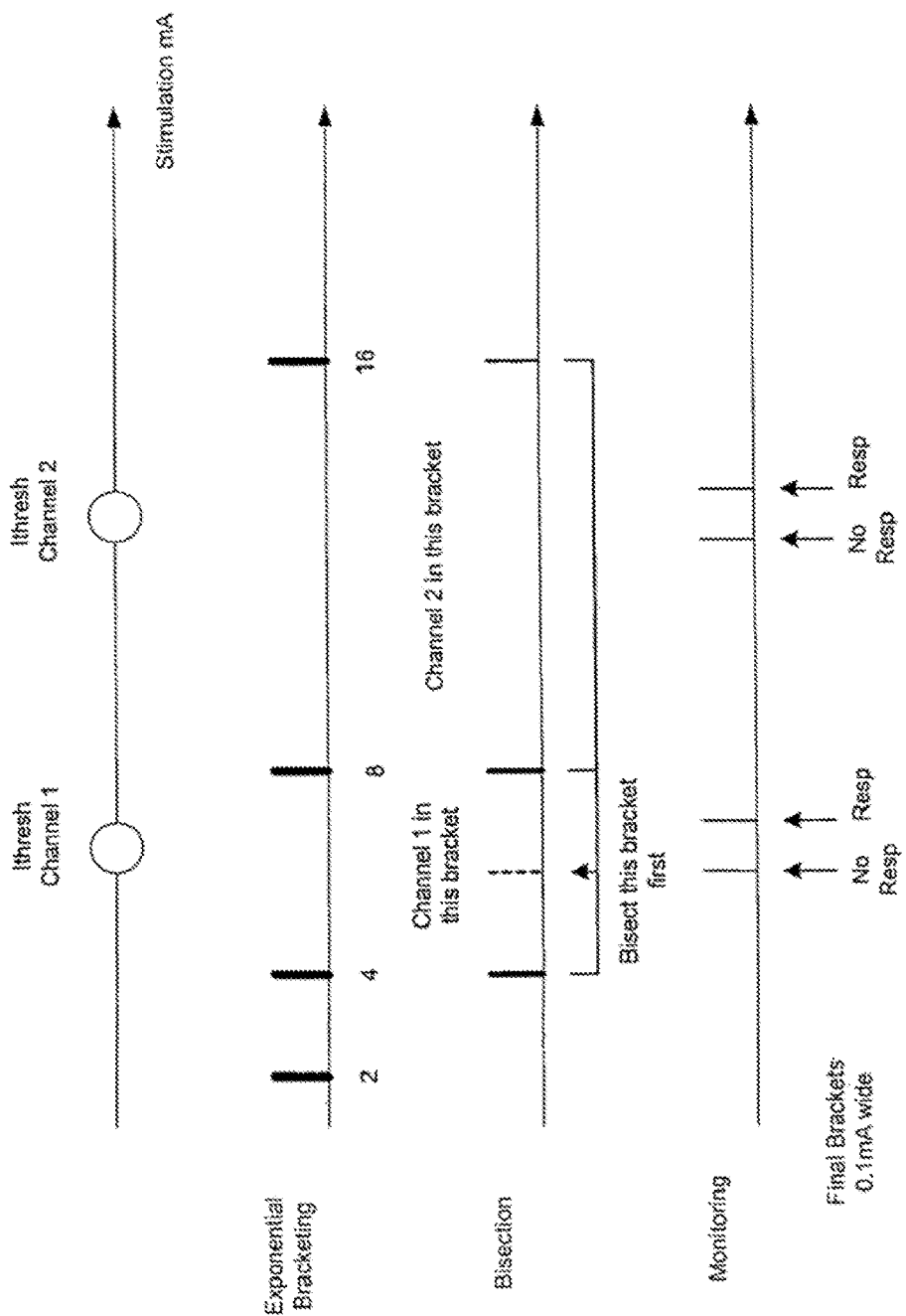
FIG. 23 is a series of graphs illustrating a multi-channel current threshold-hunting algorithm according to one embodiment of the present invention.

FIG. 20 illustrates a still further manner of performing stimulation artifact rejection according to an alternate embodiment of the present invention. This artifact rejection is premised on the characteristic delay from the stimulation current pulse to the EMG response. For each stimulation current pulse, the time from the current pulse to the first extremum (max or min) is $T_1$ and to the second extremum (max or min) is $T_2$. As will be described below, the values of $T_1$, $T_2$ are each compiled into a histogram period (see FIG. 21). New values of $T_1$, $T_2$ are acquired for each stimulation and the histograms are continuously updated. The value of $T_1$ and $T_2$ used is the center value of the largest bin in the histogram. The values of $T_1$, $T_2$ are continuously updated as the histograms change. Initially Vpp is acquired using a window that contains the entire EMG response. After 20 samples, the use of $T_1$, $T_2$ windows is phased in over a period of 200 samples. Vmax and Vmin are then acquired only during windows centered around $T_1$, $T_2$ with widths of, by way of example only, 5 msec. This method of acquiring $V_{pp}$ automatically rejects the artifact if $T_1$ or $T_2$ fall outside of their respective windows.

Having measured each Vpp EMG response (as facilitated by the stimulation and/or noise artifact rejection techniques described above), this Vpp information is then analyzed relative to the stimulation current in order to determine a relationship between the nerve and the given stimulation element transmitting the stimulation current. More specifically, the present invention determines these relationships (between nerve and the stimulation element) by identifying the minimum stimulation current ($I_{Thresh}$) capable of resulting in a predetermined Vpp EMG response. According to the present invention, the determination of $I_{Thresh}$ may be accomplished via any of a variety of suitable algorithms or techniques.

FIGS. 22A-22E illustrate, by way of example only, a threshold-hunting algorithm for quickly finding the threshold current ($I_{Thresh}$) for each nerve being stimulated by a given stimulation current ($I_{Stim}$). Threshold current ($I_{Thresh}$), once again, is the minimum stimulation current ($I_{Stim}$) that results in a Vpp that is greater than a known threshold voltage ($V_{Thresh}$). The value of is adjusted by a bracketing method as follows. The first bracket is 0.2 mA and 0.3 mA. If the Vpp corresponding to both of these stimulation currents is lower than VThresh, then the bracket size is doubled to 0.2 mA and 0.4 mA. This doubling of the bracket size continues until the upper end of the bracket results in a Vpp that is above VThresh. The size of the brackets is then reduced by a bisection method. A current stimulation value at the midpoint of the bracket is used and if this results in a Vpp that is above VThresh, then the lower half becomes the new bracket. Likewise, if the midpoint Vpp is below VThresh then the upper half becomes the new bracket. This bisection method is used until the bracket size has been reduced to $I_{Thresh}$ mA. $I_{Thresh}$ may be selected as a value falling within the bracket, but is preferably defined as the midpoint of the bracket.

The threshold-hunting algorithm of this embodiment will support three states: bracketing, bisection, and monitoring. A stimulation current bracket is a range of stimulation currents that bracket the stimulation current threshold $I_{Thresh}$. The width of a bracket is the upper boundary value minus the lower boundary value. If the stimulation current threshold $I_{Thresh}$ of a channel exceeds the maximum stimulation current, that threshold is considered out-of-range. During the bracketing state, threshold hunting will employ the method below to select stimulation currents and identify stimulation current brackets for each EMG channel in range.

The method for finding the minimum stimulation current uses the methods of bracketing and bisection. The "root" is identified for a function that has the value−1 for stimulation currents that do not evoke adequate response; the function has the value+1 for stimulation currents that evoke a response. The root occurs when the function jumps from −1 to +1 as stimulation current is increased: the function never has the value of precisely zero. The root will not be known exactly, but only with a level of precision related to the minimum bracket width. The root is found by identifying a range that must contain the root. The upper bound of this range is the lowest stimulation current $I_{Thresh}$ where the function returns the value+1, i.e. the minimum stimulation current that evokes response. The lower bound of this range is the highest stimulation current $I_{Thresh}$ where the function returns the value−1, i.e. the maximum stimulation current that does not evoke a response.

The pedicle integrity assessment function may begin by adjusting the stimulation current until the root is bracketed (FIG. 22B). The initial bracketing range may be provided in any number of suitable ranges. In one embodiment, the initial bracketing range is 0.2 to 0.3 mA. If the upper stimulation current does not evoke a response, the upper end of the range should be increased. The range scale factor is 2. The stimulation current should preferably not be increased by more than 10 mA in one iteration. The stimulation current should preferably never exceed the programmed maximum stimulation current. For each stimulation, the algorithm will examine the response of each active channel to determine whether it falls within that bracket. Once the stimulation current threshold of each channel has been bracketed, the algorithm transitions to the bisection state.

During the bisection state (FIGS. 22C and 22D), threshold hunting will employ the method described below to select stimulation currents and narrow the bracket to a selected width (for example, 0.1 mA) for each EMG channel with an in-range threshold. After the minimum stimulation current has been bracketed (FIG. 22B), the range containing the root is refined until the root is known with a specified accuracy. The bisection method is used to refine the range containing the root. In one embodiment, the root should be found to a precision of 0.1 mA. During the bisection method, the stimulation current at the midpoint of the bracket is used. If the stimulation evokes a response, the bracket shrinks to the lower half of the previous range. If the stimulation fails to evoke a response, the bracket shrinks to the upper half of the previous range. The proximity algorithm is locked on the electrode position when the response threshold is bracketed by stimulation currents separated by the selected width (i.e. 0.1 mA). The process is repeated for each of the active channels until all thresholds are precisely known. At that time, the algorithm enters the monitoring state.

After identifying the threshold current $I_{Thresh}$, this information may be employed to determine any of a variety of relationships between the screw test accessory and the nerve. For example, as will be described in greater detail below, when determining the current threshold $I_{Thresh}$ of a nerve during pedicle integrity assessment, the relationship between the pedicle testing assembly 36 and the nerve is whether electrical communication is established therebetween. If electrical communication is established, this indicates that the medial wall of the pedicle has been cracked, stressed, or otherwise breached as a result of pilot hole formation, pilot hole preparation, and/or screw introduction. If not, this indicates that the integrity of the medial wall of the pedicle has remained intact. This characteristic is based on the insulating properties of bone.

In a significant aspect of the present invention, the relationships determined above based on the current threshold determination may be communicated to the user in an easy to use format, including but not limited to, alpha-numeric and/or graphical information regarding pedicle integrity assessments, stimulation level, EMG responses, instrument in use, set-up, and related instructions for the user. This advantageously provides the ability to present simplified yet meaningful data to the user, as opposed to the actual EMG waveforms that are displayed to the users in traditional EMG systems. Due to the complexity in interpreting EMG waveforms, such prior art systems typically require an additional person specifically trained in such matters which, in turn, can be disadvantageous in that it translates into extra expense (having yet another highly trained person in attendance) and oftentimes presents scheduling challenges because most hospitals do not retain such personnel.

When employed in spinal procedures, for example, such EMG monitoring would preferably be accomplished by connecting the EMG harness 26 to the myotomes in the patient's legs corresponding to the exiting nerve roots associated with the particular spinal operation level. In a preferred embodiment, this is accomplished via 8 pairs of EMG electrodes 27 placed on the skin over the major muscle groups on the legs (four per side), an anode electrode 29 providing a return path for the stimulation current, and a common electrode 31 providing a ground reference to pre-amplifiers in the patient module 24. Although not shown, it will be appreciated that any of a variety of electrodes can be employed, including but not limited to needle electrodes. The EMG responses measured via the EMG harness 26 provide a quantitative measure of the nerve depolarization caused by the electrical stimulus. By way of example, the placement of EMG electrodes 27 may be undertaken according to the manner shown in Table 1 below for spinal surgery:

TABLE 1

| Color | Channel ID | Myotome | Spinal Level |
|---|---|---|---|
| Blue | Right 1 | Right Vastus Medialis | L2, L3, L4 |
| Violet | Right 2 | Right Tibialis Anterior | L4, L5 |
| Grey | Right 3 | Right Biceps Femoris | L5, S1, S2 |
| White | Right 4 | Right Gastroc. Medial | S1, S2 |
| Red | Left 1 | Left Vastus Medialis | L2, L3, L4 |
| Orange | Left 2 | Left Tibialis Anterior | L4, L5 |
| Yellow | Left 3 | Left Biceps Femoris | L5, S1, S2 |
| Green | Left 4 | Left Gastroc. Medial | S1, S2 |

Figure 24:
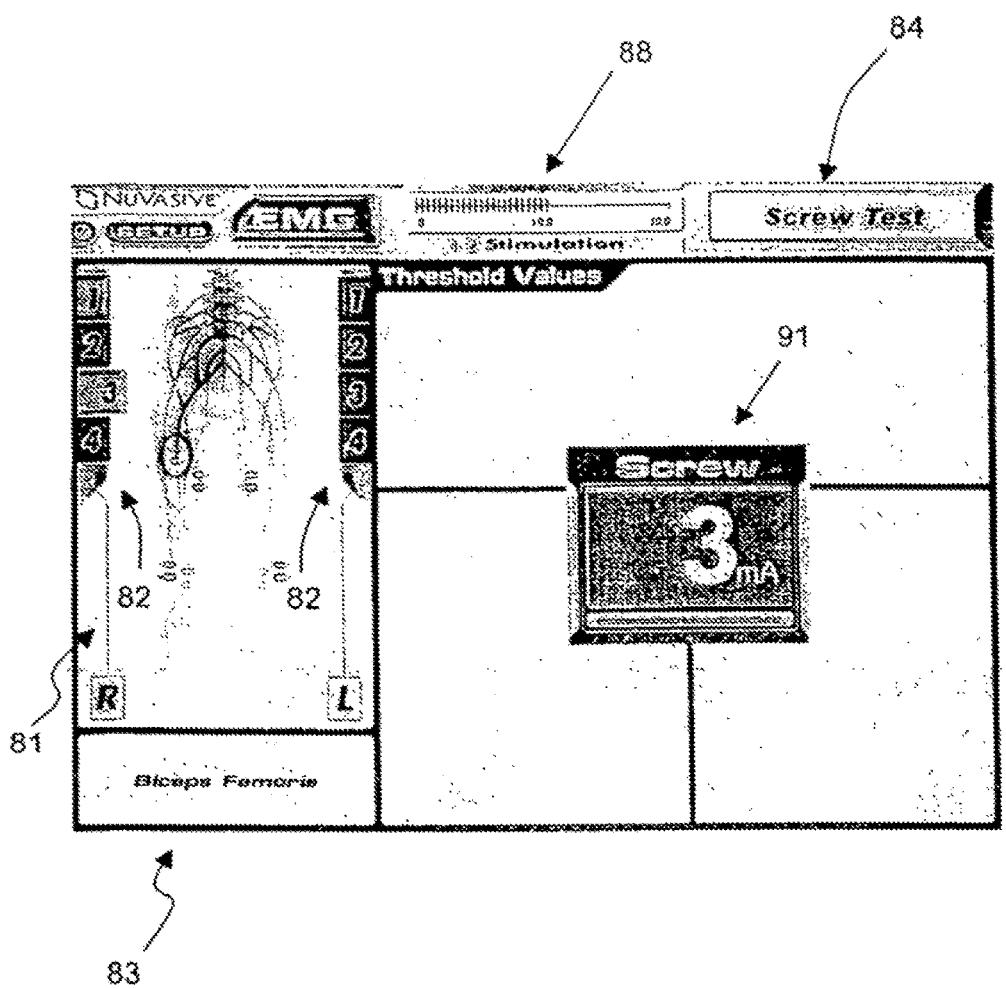
FIGS. 24-25 are exemplary screen displays illustrating one embodiment of the pedicle integrity assessment feature of the present invention.
Figure 25:
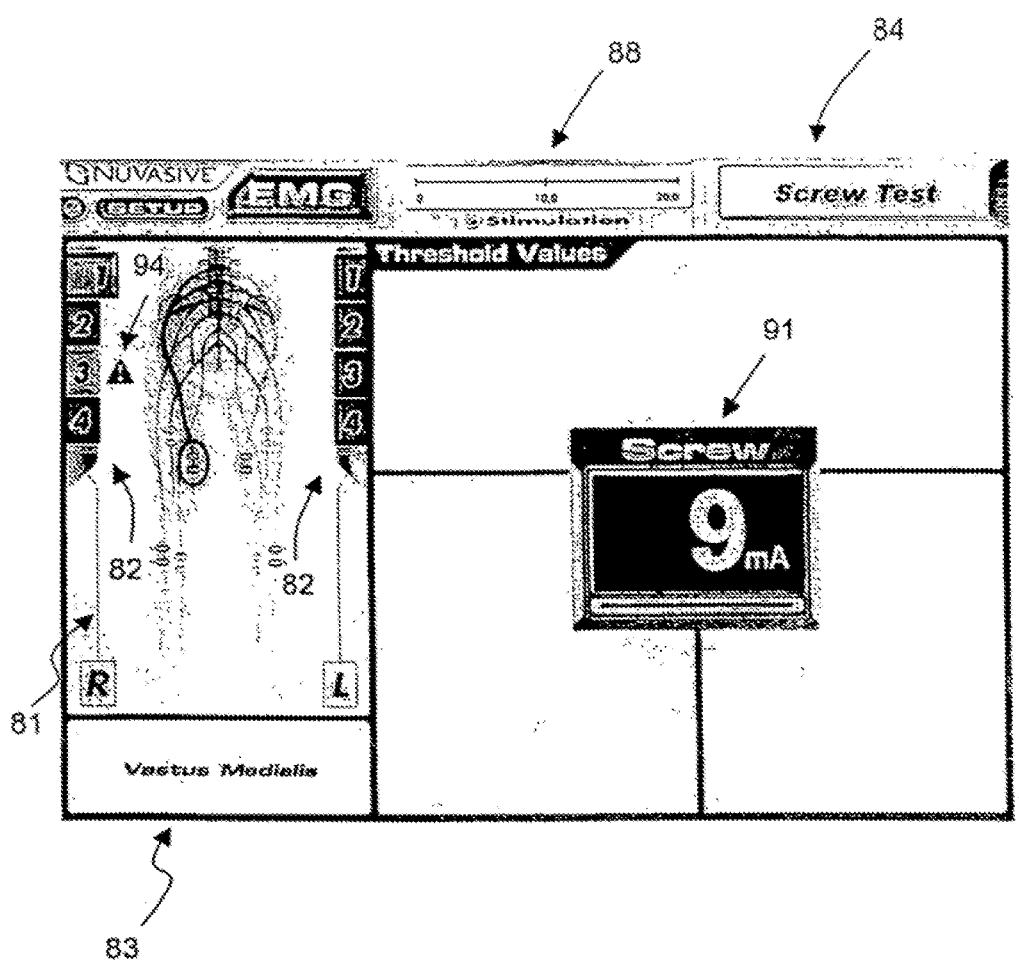
Figure 26:
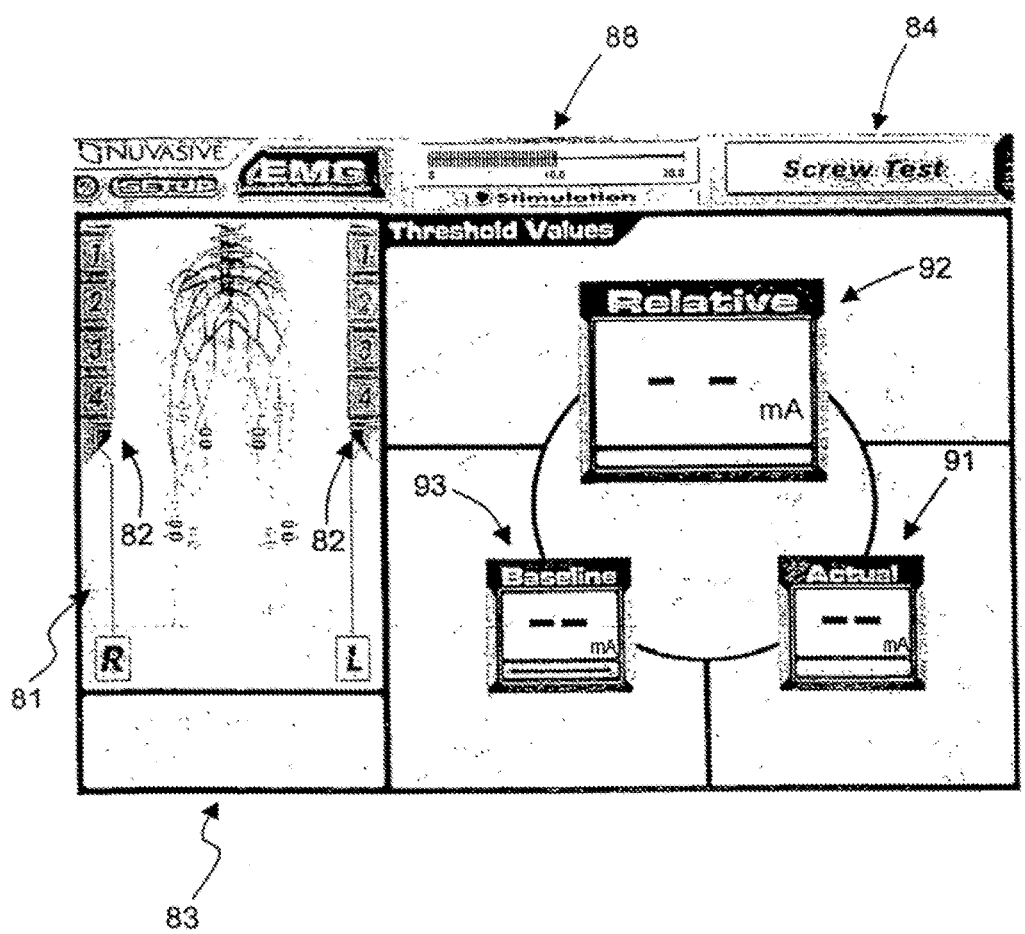
FIGS. 26-28 are exemplary screen displays illustrating another embodiment of the pedicle integrity assessment feature of the present invention.
Figure 27:
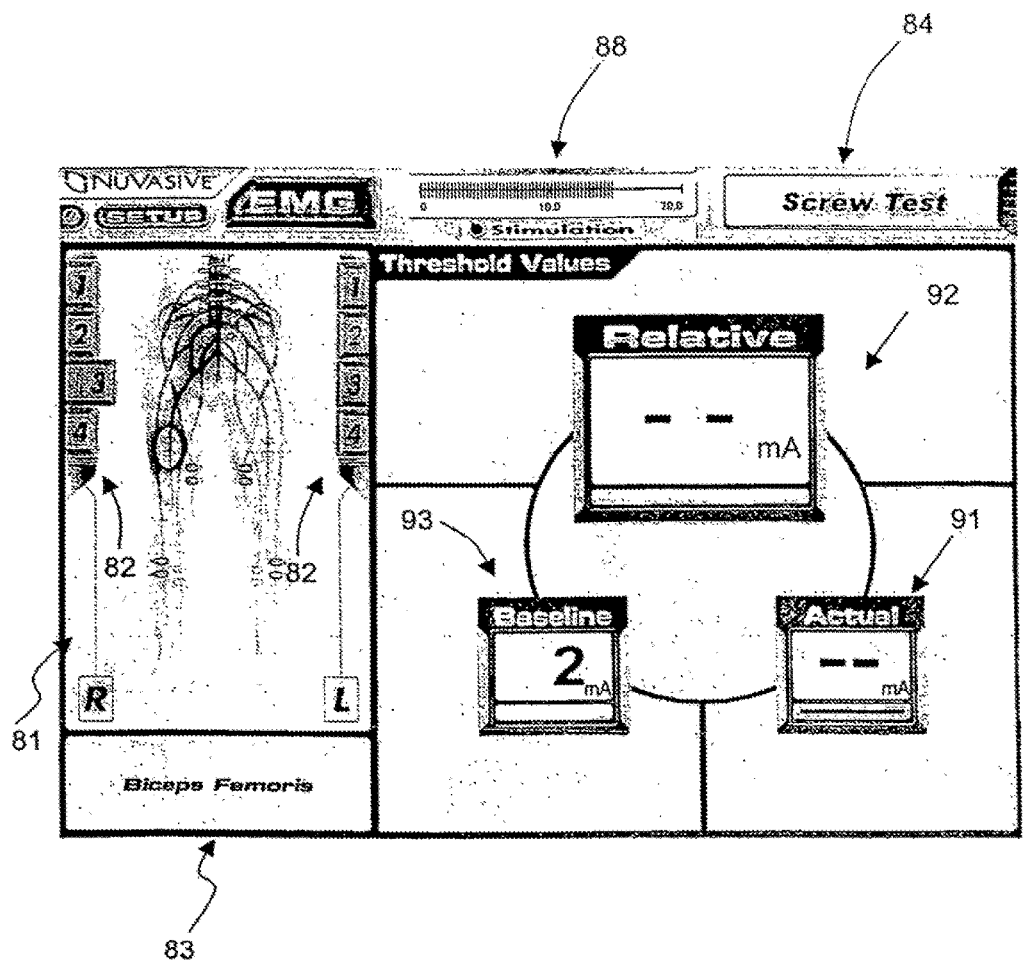
Figure 28:
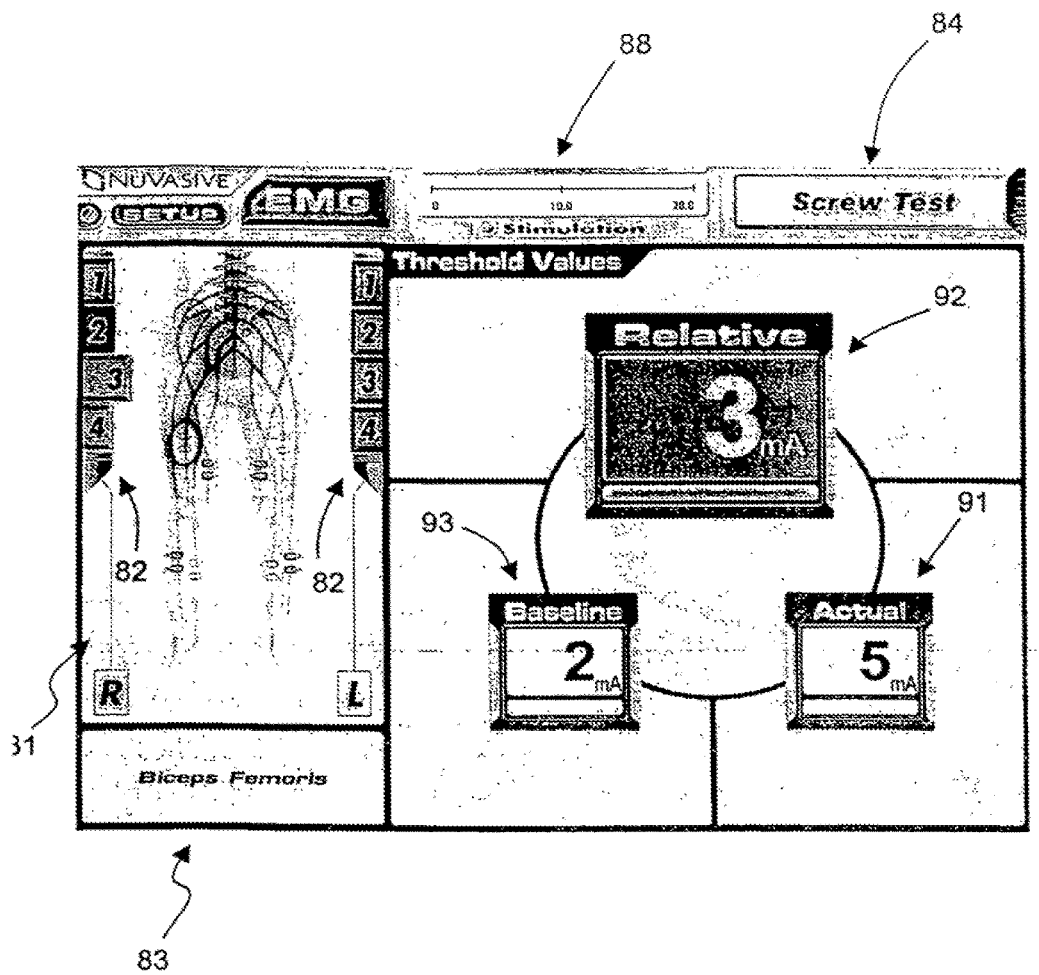

With reference again to FIGS. 2-3, the surgical system 20 performs pedicle integrity assessments via, by way of example only, the use of pedicle testing accessories 30 in combination with the handle assembly 36. More specifically, upon pressing the button on the screw test handle 36, the software will execute a testing algorithm to apply a stimulation current to the particular target (i.e. pilot hole, inserted pedicle screw, or bare nerve), setting in motion the pedicle integrity assessment function of the present invention. The pedicle integrity assessment features of the present invention may include, by way of example only, an "Actual" mode (FIGS. 24-25) for displaying the actual stimulation threshold 91 measured for a given myotome, as well as a "Relative" mode (FIGS. 26-28) for displaying the difference 92 between a baseline stimulation threshold assessment 93 of a bare nerve root and an actual stimulation threshold assessment 91 for a given myotome. In either case, the surgical accessory label 84 displays the word "SCREW TEST" to denote use of the pedicle testing assembly 36 for performing pedicle integrity assessments. The screw test algorithm according to the present invention preferably determines the depolarization (threshold) current for all responding EMG channels. In one embodiment, the EMG channel tabs 82 may be configured such that the EMG channel having the lowest stimulation threshold will be automatically enlarged and/or highlighted and/or colored (EMG channel tab R3 as shown in FIG. 24) to clearly indicate this fact to the user. As shown in FIG. 25, this feature may be overridden by manually selecting another EMG channel tab (such as EMG channel tab R1 in FIG. 25) by touching the particular EMG channel tab 82 on the touch screen display 40. In this instance, a warning symbol 94 may be provided next to the EMG channel tab having the lowest stimulation threshold (once again, EMG channel tab R3 in FIG. 24) to inform the user that the stimulation threshold 91 is not the lowest stimulation threshold.

Any number of the above-identified indicia (such as the baseline stimulation 93, actual stimulation 91, difference 92, and EMG channel tabs 82) may be color-coded to indicate general safety ranges (i.e. "green" for a range of stimulation thresholds above a predetermined safe value, "red" for range of stimulation thresholds below a predetermined unsafe value, and "yellow" for the range of stimulation thresholds in between the predetermined safe and unsafe values—designating caution). In one embodiment, "green" denotes a stimulation threshold range of 9 milliamps (mA) or greater, "yellow" denotes a stimulation threshold range of 6-8 mA, and "red" denotes a stimulation threshold range of 6 mA or below. By providing this information graphically, a surgeon may quickly and easily test to determine if the integrity of a pedicle has been breached or otherwise compromised, such as may result due to the formation of a pedicle screw hole and/or introduction of a pedicle screw. More specifically, if after stimulating the screw hole and/or pedicle screw itself the stimulation threshold is: (a) at or below 6 mA, the threshold display 40 will illuminate "red" and thus indicate to the surgeon that a breach is likely; (b) between 6 and 8 mA, the threshold display 40 will illuminate "yellow" and thus indicate to the surgeon that a breach is possible; and/or (c) at or above 8 mA, the threshold display 40 will illuminate "green" and thus indicate to the surgeon that a breach is unlikely. If a breach is possible or likely (that is, "yellow" or "red"), the surgeon may choose to withdraw the pedicle screw and redirect it along a different trajectory to ensure the pedicle screw no longer breaches (or comes close to breaching) the medial wall of the pedicle.

While this invention has been described in terms of a best mode for achieving this invention's objectives, it will be appreciated by those skilled in the art that variations may be accomplished in view of these teachings without deviating from the spirit or scope of the present invention. For example, the present invention may be implemented using any combination of computer programming software, firmware or hardware. As a preparatory step to practicing the invention or constructing an apparatus according to the invention, the computer programming code (whether software or firmware) according to the invention will typically be stored in one or more machine readable storage mediums such as fixed (hard) drives, diskettes, optical disks, magnetic tape, semiconductor memories such as ROMs, PROMs, etc., thereby making an article of manufacture in accordance with the invention. The article of manufacture containing the computer programming code is used by either executing the code directly from the storage device, by copying the code from the storage device into another storage device such as a hard disk, RAM, etc. or by transmitting the code on a network for remote execution. As can be envisioned by one of skill in the art, many different combinations of the above may be used and accordingly the present invention is not limited by the scope of the appended claims.

What is claimed is:

1. A system for performing percutaneous pedicle integrity during spine surgery, comprising:
   a stimulation element comprising a tubular insulation member with a longitudinal lumen therethrough, which is configured for percutaneous introduction to a pedicle target site within a patient and a K-wire which is disposed through the lumen of the insulation member, and having a stimulation region at a distal end which extends from a distal end of the insulation member and which is configured for contacting at least one of a pilot hole formed in said pedicle and a screw implanted in said pedicle; and
   a control unit in electrical communication with said stimulation element, said control unit configured for selectively applying a stimulation signal to said stimulation element, providing an assessment of whether nerves adjacent said pedicle target site innervate as a result of applying said stimulation signal to said element, and communicating the assessment to a user, wherein selectively applying the stimulation signal to said stimulation element comprises identifying a minimum stimulation current capable of evoking a predetermined peak-to-peak voltage associated with a neuromuscular response, wherein providing the assessment also includes determining a relationship between the identified minimum stimulation current and the predetermined peak-to-peak voltage associated with the neuromuscular response to indicate a pedicle integrity based on contact of the distal end of the K-wire at the at least one of a pilot hole formed in said pedicle and a screw implanted in said pedicle.

2. The system of claim 1 and further, wherein said insulation member includes an electrical coupling mechanism for establishing electrical contact between said stimulation source and said stimulation element.

3. The system of claim 2 and further, wherein said electrical coupling mechanism is a clip that attaches directly to an uninsulated portion near a proximal end of said K-wire.

4. The system of claim 1 and further, wherein said control unit comprises an EMG monitoring system for assessing whether nerves adjacent said pedicle target site innervate as a result of applying said stimulation signal to said stimulation element.

5. The system of claim 4 and further, wherein said EMG monitoring system displays at least one of alpha-numeric and graphical information to a user regarding whether nerves adjacent said pedicle target site innervate as a result of applying said stimulation signal to said stimulation element.

6. A system for performing percutaneous pedicle integrity assessments during spine surgery, comprising:
   a stimulation element comprising a tubular insulation member with a longitudinal lumen therethrough, positionable within a patient and configured for percutaneous introduction to and contact with one of a fully inserted pedicle screw and an interior of a pedicle screw pilot hole in said patient, said lumen dimensioned to receive and pass through a pedicle preparation tool having an uninsulated stimulation region at a distal end; and
   a control unit in electrical communication with said stimulation region, said control unit configured for selectively applying a stimulation signal to said stimulation region, providing an assessment of whether nerves adjacent said pedicle target site innervate as a result of applying said stimulation signal to said stimulation region, and communicating said assessment to a user, wherein selectively applying the stimulation signal to said stimulation element comprises identifying a minimum stimulation current capable of evoking a predetermined peak-to-peak voltage associated with a neuromuscular response, wherein providing the assessment also includes determining a relationship between the identified minimum stimulation current and the predetermined peak-to-peak voltage associated with the neuromuscular response to indicate a pedicle integrity based on contact of the distal end of the stimulation element at the at least one of a pilot hole formed in said pedicle and a screw implanted in said pedicle.

7. The system of claim 6 and further, wherein said pedicle preparation tool is a tap.

8. The system of claim 6 and further, wherein said insulation member is a universal insulating unit.

9. The system of claim 6 and further, wherein said insulation member includes an electrical coupling mechanism for establishing electrical contact between said stimulation source and said stimulation element.

10. The system of claim 9 and further, wherein said electrical coupling mechanism is a clip that attaches directly to an uninsulated portion near a proximal end of said pedicle preparation tool.

11. The system of claim 6 and further, wherein said control unit comprises an EMG monitoring system for assessing whether nerves adjacent said pedicle target site innervate as a result of applying said stimulation signal to said preparation tool.

12. The system of claim 11 and further, wherein said EMG monitoring system displays at least one of alpha-numeric and graphical information to a user regarding whether nerves adjacent said pedicle target site innervate as a result of applying said stimulation signal to said stimulation region.

* * * * *